United States Patent
Rouet et al.

(10) Patent No.: US 10,272,135 B2
(45) Date of Patent: Apr. 30, 2019

(54) APOLIPOPROTEIN O AND FRAGMENTS THEREOF FOR INDUCING APOPTOSIS IN A CANCEROUS CELL

(71) Applicants: INSERM (INSTITUT NATIONAL DE LA SANTÉ ET DE LA RECHERCHE MÉDICALE), Paris (FR); UNIVERSITE PAUL SABATIER TOULOUSE III, Toulouse (FR)

(72) Inventors: Philippe Rouet, Toulouse (FR); Fatima Smih, Toulouse (FR)

(73) Assignees: Philippe Rouet, Clermont le Fort (FR); Fatima Smih-Rouet, Clermont le Fort (FR)

( * ) Notice: Subject to any disclaimer, the term of this patent is extended or adjusted under 35 U.S.C. 154(b) by 0 days.

(21) Appl. No.: 15/304,160

(22) PCT Filed: Apr. 15, 2015

(86) PCT No.: PCT/EP2015/058143
§ 371 (c)(1),
(2) Date: Oct. 14, 2016

(87) PCT Pub. No.: WO2015/158760
PCT Pub. Date: Oct. 22, 2015

(65) Prior Publication Data
US 2017/0035842 A1     Feb. 9, 2017

(30) Foreign Application Priority Data

Apr. 16, 2014   (EP) .................................... 14305565

(51) Int. Cl.
*A61K 38/17*    (2006.01)
*C07K 16/18*    (2006.01)

(52) U.S. Cl.
CPC ...... *A61K 38/1709* (2013.01); *A61K 38/1716* (2013.01); *C07K 16/18* (2013.01)

(58) Field of Classification Search
None
See application file for complete search history.

(56) References Cited

U.S. PATENT DOCUMENTS

2013/0336797 A1* 12/2013 Wang ...................... F04D 29/34
                                                           416/214 R
2015/0368715 A1* 12/2015 Smih ..................... C12Q 1/6883
                                                           424/135.1

FOREIGN PATENT DOCUMENTS

| WO | 2012/072681 A1 | 6/2012 |
| WO | 2013/183964 A1 | 12/2013 |

OTHER PUBLICATIONS

A.E.Turkhieh, Contribution à l'étude du rôle physiologique de l'apolipoprotéine O, doctoral thesis retrieved from internet: <http://www.theses.fr/2012TOU30073> [retrieved on Nov. 27, 2017] . 2012, abstract only.*

(Continued)

*Primary Examiner* — Claire Kaufman
(74) *Attorney, Agent, or Firm* — W&C IP

(57) ABSTRACT

The invention relates to a compound for use for inducing apoptosis in a cancerous cell, wherein said compound is selected from the group consisting of ApoO, a variant or a fragment thereof, their mixtures, and a vector encoding for said ApoO, variant or fragment thereof. The invention further relates to a compound for use for treating a pathophysiological situation, wherein said compound is an inhibitor of the ApoO activity or of the ApoO gene expression.

Figure 1:
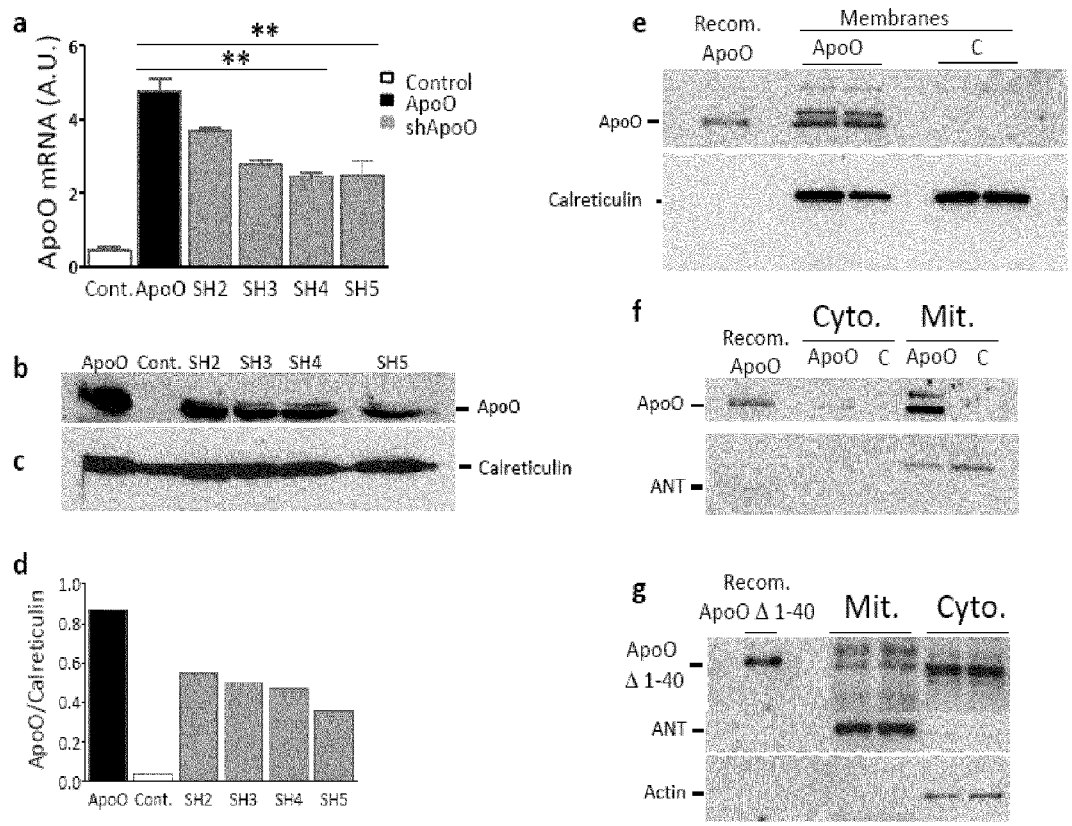

19 Claims, 12 Drawing Sheets
Specification includes a Sequence Listing.

(56) References Cited

OTHER PUBLICATIONS

Turkieh Annie et al: "Apolipoprotein 0 is mitrochondrial and promotes lipotoxicity in heart.", The Journal of Clinical Investigation May 1, 2014, vol. 124, No. 5, May 1, 2014 pp. 2277-2286.
Chen-Lu Wu et al: "Microarray analysis provides new insights into the function of apolipoprotein 0 in HepG2 cell line", Lipids in Health and Disease, Biomed Central, London, GB. vol. 12, No. 1, Dec. 17, 2013, p. 186.
Matthieu Lamant et al: "ApoO, a Novel Apolipoprotein, Is an Original Glycoprotein Up-regulated by Diabetes in Human Heart", Journal of Biological Chemistry, American Society for Biochemistry and Molecular Biology, US, vol. 281, No. 47, Nov. 24, 2006, pp. 36289-36302.

* cited by examiner

A  B

Without ApoO +Palmitate    With ApoO + Palmitate

Without ApoO         With ApoO

APOLIPOPROTEIN O AND FRAGMENTS THEREOF FOR INDUCING APOPTOSIS IN A CANCEROUS CELL

FIELD OF THE INVENTION

The invention relates to a compound for use for inducing apoptosis in a cancerous cell, wherein said compound is selected from the group consisting of Apolipoprotein O (ApoO), a variant or a fragment thereof, their mixtures, and a vector encoding for said ApoO, variant or fragment thereof.

BACKGROUND OF THE INVENTION

The epidemic of cancer dramatically spread those last decades and indisputably became the main studied disease of current times. New aspects of the genetics of cancer pathogenesis are increasingly recognized as important. Novel strategies were recently developed for treating patients suffering from cancer. Among them, novel chemotherapy compounds were designed for inducing cell cycle arrest or inducing apoptosis. Indeed, inducing apoptosis became a highly promising strategy for treating patients. However, the scientific community is avidly in need for new compounds which alleviate the well-known side effects of current chemotherapies and provide efficient results in the treatment of cancer.

On the other hand, the epidemic of obesity and diabetes has reached worldwide proportions, and are forerunner of secondary organ failure through exogenous lipid deposition in nonadipose tissues, thereby leading to premature death. Indeed, frequent disorders associated with obesity (nonalcoholic fatty liver disease, type 2 diabetes, and lipotoxic cardiomyopathy) are attributed to excess lipid accumulation in organs, a pathologic process that has been termed lipotoxicity. However, the mechanism responsible for said lipotoxicity is still at debate and no efficient therapy for treating pathologies attributed to excess lipid accumulation was found to be appropriate to date. There is thus a long unfulfilled need for new therapeutic strategies for treating and/or preventing pathologies attributed to excess lipid accumulation.

SUMMARY OF THE INVENTION

The inventors have shown that ApoO localizes within mitochondria and that its expression is associated with mitochondrial dysfunction, especially in murine and human heart. They evidenced that ApoO interacts with adenine nucleotide translocase (ANT) and cyclophillin D (CypD) and causes the mitochondrial permeability transition pore (MPTP) to adopt an open state, which induces mild uncoupling.

Consequently, mitochondrial respiration and fatty acid metabolism are enhanced. This cascade of events generates a mitochondrial metabolic sink whereby cells accumulate lipids and lipotoxic products, finally leading to apoptosis.

Therefore, the inventors have surprisingly shown a new role of ApoO, highly useful for developing new therapeutic strategies for treating cancer, more precisely for inducing apoptosis in cancerous cells. The invention thus relates to a compound for use for inducing apoptosis in a cancerous cell, wherein said compound is selected from the group consisting of ApoO, a variant or a fragment thereof, their mixtures, and a vector encoding for said ApoO, variant or fragment thereof.

More precisely, by experimenting on murine and human hearts, the inventors found that overexpression of ApoO induces cardiomyopathy, mimicking the metabolic phenotype of the diabetic heart. The invention thus also relates to a compound for use in a method for reducing lipid overload in a pathophysiological situation, preferably in obesity, diabetes, cardiomyopathy, myopathy, fatty liver, pancreatitis, and/or hypothyroidism, wherein said compound is an inhibitor of the ApoO activity or of the ApoO gene expression.

DETAILED DESCRIPTION OF THE INVENTION

Definitions

Throughout the specification, several terms are employed and are defined in the following paragraphs.

As used herein, the term "Apolipoprotein O" or "ApoO" has its general meaning in the art and denotes a member of the Apolipoprotein proteins family that binds to lipids to form lipoproteins, which transport the lipids through the lymphatic and circulatory systems. ApoO is a 198-amino acid protein that contains an N-terminal 23-amino acid long signal peptide. Its sequence is as follows:

MFKVIQRSVGPASLSLLTFKVYAAPKKDSPPKNSVKVDELSLYSVPEG

QSKYVEEARSQLEESISQLRHYCEPYTTWCQETYSQTKPKMQSLVQWGL

DSYDYLQNAPPGFFPRLGVIGFAGLIGLLLARGSKIKKLVYPPGFMGLA

ASLYYPQQAIVFAQVSGERLYDWGLRGYIVIEDLWKENFQKPGNVKNSP

GTK.

Said sequence is depicted by SEQ ID NO: 1.

The ApolipoproteinO gene is expressed in a set of human tissues. An exemplary sequence for human ApoO gene is deposited in the database under accession number NM_024122. An exemplary sequence for human ApoO protein is deposited in the UniProtKB/Swiss-Prot database under accession number Q9BUR5.

As used herein, the expressions "mitochondrial permeability transition pore" or "MPTP" refer to a pore localized on the mitochondrial membrane. This pore enables free passage into the mitochondria of metabolites and molecules of molecular mass below 1.5 kDa including protons. The proteins which constitute the MPTP include at least the voltage-dependent anion channels (VDAC), cyclophillin D (CypD), and adenine nucleotide translocase (ANT), the latter acting as a regulator of MPTP opening.

As used herein, the expressions "mitochondrial uncoupling" and "uncoupling" refer to the phenomenon causing the mitochondrial proton gradient to be dissipated before it can serve its purpose to provide the energy for oxidative phosphorylation.

As used herein, the term "apoptosis" refers to a programmed cell death. In the context of the invention, said death is induced by ApoO through a new biological process evidenced by the inventors. Said process involves the opening of the MPTP inducing an uncoupling, eventually leading to an accumulation of lipid and lipotoxic products, and therefore to apoptosis.

As used herein, the expression "Caspase 3" refers to a caspase protein that interacts with caspase 8 and caspase 9. It is encoded by the CASP3 gene. Caspase-3 is activated in the apoptotic cell both by extrinsic (death ligand) and intrinsic (mitochondrial) pathways.

In its broadest meaning, the terms "treating" or "treatment" refer to reversing, alleviating, inhibiting the progress of, or preventing the disorder or condition to which such term applies, or one or more symptoms of such disorder or condition.

Treatment of Cancer

In a first aspect, the invention relates to a compound for use for inducing apoptosis in a cancerous cell, wherein said compound is selected from the group consisting of ApoO, a variant or a fragment thereof, their mixtures, and a vector encoding for said ApoO, variant or fragment thereof.

The invention also relates to a compound for use for treating cancer, by inducing apoptosis in a cancerous cell, wherein said compound is selected from the group consisting of ApoO, a variant or a fragment thereof, their mixtures, and a vector encoding for said ApoO, variant or fragment thereof.

The term "cancer" refers to a disease or disorder that is characterized by unregulated cell growth, also referred to as cancerous cells.

The inventors have shown, for the very first time, a new role of the protein ApoO. By performing in vivo fluorescent labelling of ApoO in cardiac myoblasts, the inventors evidenced an unexpectedly localization within the mitochondria of ApoO. Indeed, ApoO is addressed to the inner mitochondrial membrane.

They then evidenced that ApoO plays a key role in the regulation of mitochondrial function and energy generation. For fulfilling said purpose, ApoO has privileged binding partners: CypD and ANT. The inventors have shown that the interaction of ApoO with CypD and ANT leads to the opening of MPTP. MPTP is thus a main player in the regulation of mitochondrial respiration. The inventors further showed that ApoO overexpression leads to an increase in intracellular reactive oxygen species (ROS). Indeed, the mRNA levels of the proapoptotic factor Bax (Bad, Bak, Caspase-9) were enhanced. This was actually confirmed in in vivo transfected livers with the ApoO expression vector and in vitro in cardiac myoblasts.

The inventors showed that triglyceride levels were not significantly modified whereas diglyceride and ceramide levels were increased by expression of ApoO. Therefore, ApoO was shown to lead to intracellular accumulation of lipotoxic species, indisputably leading to apoptosis. Through this newly discovered biological mechanism, the opening of MPTP caused by ApoO was found to be the key step in the process of programmed cell death.

Further, the inventors developed cancerous cell lines overexpressing ApoO and they showed a significant increase in the Caspase-3 activity in said cells, indicating an increase of the apoptosis. The inventors have thus shown the role of ApoO in the induction of apoptosis in cancerous cells line, clearly evidencing that ApoO is a key target for treating cancer.

Preferably, said cancerous cell is a cell having a high content of mitochondria. Preferably, said cancerous cell comprises at least 30%, preferably 40% of mitochondria in volume.

Typically, such cancer cell is selected from the group consisting of heart cell, liver cell, bladder cell, brain cell, breast cell, colon cell, rectum cell, endometrium cell, kidney cell, blood cell, lung cell, epidermis cell, pancreas cell, prostate cell and thyroid cell.

The compound of the invention is thus highly useful for treating a cancer selected from the group consisting of heart cancer, liver cancer, bladder cancer, brain cancer, colorectal cancer, endometrial cancer, kidney cancer, leukemia, lung cancer, melanoma, lymphoma, pancreatic cancer, prostate cancer and thyroid cancer.

Preferably, said cancer is selected from the group consisting of heart cancer, liver cancer, bladder cancer, brain cancer, colorectal cancer, endometrial cancer, kidney cancer, leukemia, melanoma, lymphoma, pancreatic cancer, prostate cancer and thyroid cancer.

More preferably, said cancer is a brain cancer. Said brain cancer may be benign or malignant cancer. A non-limiting list of brain cancers includes chordomas, craniopharyngiomas, gangliocytomas, gangliomas, anaplastic gangliogliomas, glomus jugulare, meningiomas, pineocytomas, pituitary adenomas, schwannomas, glioma, hemangioblastomas and rhabdoid tumors.

Preferably, said cancer is a glioma. Gliomas are the most prevalent type of adult brain tumor, accounting for 78 percent of malignant brain tumors. They arise from the supporting cells of the brain, called the glia. These cells are subdivided into astrocytes, ependymal cells and oligodendroglial cells (or oligos). Glial tumors include the following: astrocytomas, ependymomas, glioblastoma multiforme, medulloblastomas, oligodendrogliomas.

More preferably, said cancer is glioblastoma. Glioblastoma is a rapidly progressing fatal cancer is the most common and most aggressive malignant primary brain tumor in humans, accounting for 52% of all functional tissue brain tumor cases and 20% of all intracranial tumors. The inventors evidenced that overexpression of ApoO in glioblastoma cells induces lipotoxicity and mitochondrial dysfunction. Said phenomenon eventually leads to the apoptosis of the cells.

Consequently, the invention further relates to a compound for use for treating cancer by inducing lipotoxicity and mitochondrial dysfunction in a cancerous cell, wherein said compound is selected from the group consisting of ApoO, a variant or a fragment thereof, their mixtures, and a vector encoding for said ApoO, variant or fragment thereof. By inducing lipotoxicity and mitochondrial dysfunction within cancerous cells, the compound of the invention eventually induces apoptosis of said cancerous cell.

Typically, the cancerous cells of said cancer require and/or produce high amounts of ATP. Said cells are characterized by a high oxidative phosphorylation, i.e. an enhanced metabolic activity for producing adenosine triphosphate (ATP).

Preferably, said compound is human ApoO, preferably a native human ApoO. More preferably, said compound is the sequence disclosed in SEQ ID NO: 1.

Preferably, said compound interacts with MPTP, driving MPTP to adopt an open state hereby inducing mitochondrial uncoupling. Typically, said compound interacts with the lipid or protein components of MPTP.

More preferably, said compound interacts with CypD and ANT, driving the MPTP to adopt an open state hereby inducing mitochondrial uncoupling. Said open state of MPTP enhanced the oxygen consumption and electron transport chain flux that results in an increased generation of ROS.

Preferably, said compound increases mitochondrial respiration, increases fatty acid metabolism and induces lipid accumulation within said cancerous cells. Those phenomena undeniably lead to the apoptosis of the cancerous cell.

As used herein, the expression "ApoO variants" refers to proteins that are functional equivalents to a native sequence ApoO that have similar amino acid sequences and retain, to some extent, one or more activities of the native ApoO for inducing cellular lipotoxicity. Variants also include ApoO fragments that retain activity. Such variants include proteins having amino acid alterations such as deletions, insertions and/or substitutions. A "deletion" refers to the absence of one or more amino acid residues in the related protein. The term "insertion" refers to the addition of one or more amino acids in the related protein. A "substitution" refers to the replacement of one or more amino acid residues by another amino acid residue in the polypeptide. Typically, such alterations are conservative in nature such that the activity of the variant protein is substantially similar to a native sequence protein (see, e.g., Creighton (1984) Proteins, W.H. Freeman and Company). In the case of substitutions, the amino acid replacing another amino acid usually has similar structural and/or chemical properties. Insertions and deletions are typically in the range of 1 to 5 amino acids, although depending upon the location of the insertion, more amino acids can be inserted or removed. The variations can be made using methods known in the art such as site-directed mutagenesis (Carter, et al. 1985; Nucl. Acids Res. 13:4331; Zoller et al. 1982), cassette mutagenesis (Wells et al. 1985), and PCR mutagenesis (Sambrook et al., Molecular Cloning: A Laboratory Manual, 3rd edition, Cold Spring Harbor Press, N.Y., (2001)).

Preferably, ApoO variants comprise an amino acid sequence comprising at least 70% amino acid sequence identity, preferably at least 75%, 80%, 85%, 90%, 95% or 97% amino acid sequence identity over ApoO native amino acid sequence.

By "percent (%)amino acid sequence identity" refers to the percentage of amino acid residues in a candidate sequence that are identical with the amino acid residues in a ApoO sequence, after aligning the sequences and introducing gaps, if necessary, to achieve the maximum percent sequence identity, and not considering any conservative substitutions as part of the sequence identity.

As used herein, the expression "ApoO fragment" refers to a polypeptide which may retain essentially the same biological function or activity of native ApoO and which comprises a region of ApoO amino acid sequence. Preferably, said fragment has a length comprised between 30 to 190, preferably between 40 and 160, and more preferably between 70 and 160 amino acids.

Preferably, said fragment comprises at least 8 amino acids, preferably at least 9 amino acids, preferably at least 10 amino acids, preferably at least 15 amino acids, preferably at least 20 amino acids, or preferably at least 30 amino acids.

Preferably, said fragment has a length comprised between 8 and 190, preferably between 8 and 100, and more preferably between 8 and 50 amino acids.

Indeed, the inventors have evidenced that ApoO sequence comprise an N-terminal mitochondrial address label comprising 40 N-terminal amino acids. Those amino acids are thus essential for the ApoO fragment to be correctly addressed to the mitochondrial membrane.

Alternatively, said fragment comprises at least 60, preferably 90, preferably 120, or preferably 158 C-terminal amino acids of the native ApoO. Preferably, said fragment is selected from the group consisting of the fragments depicted in SEQ ID NO:10, SEQ ID NO:11 and SEQ ID NO:12.

Said fragments are respectively as follows:

```
SEQ ID No 10:
YTTWCQETY;

SEQ ID No 11:
QWGLDSYDY;
and

SEQ ID No 12:
YDWGLRGY.
```

More preferably, said fragment is the fragment depicted in SEQ ID NO: 12.

Without being bound to any theory, the inventors believe these very specific fragments of ApoO are responsible for the valuable properties of ApoO in the context of this invention.

Typically, said ApoO or ApoO fragment may be in a vector. A "vector" is a nucleic acid that is capable of transporting another nucleic acid. Vectors may be, for example, plasmids, cosmids or phage. A vector is capable of directing expression of a protein encoded by one or more genes carried by the vector when it is present in the appropriate environment. The vector generally comprises the gene that encodes a protein that is desirably expressed in one or more target cells. Preferably, the gene of interest is located between the 5' LTR and 3' LTR sequences. Further, the gene of interest is preferably in a functional relationship with other genetic elements, for example transcription regulatory sequences such as promoters and/or enhancers, to regulate expression of the gene of interest in a particular manner once the gene is incorporated into the target cell. In certain embodiments, the useful transcriptional regulatory sequences are those that are highly regulated with respect to activity, both temporally and spatially. The person skilled in the art is aware of the routine techniques for carefully selecting a vector and implementing the expression of ApoO within the target cancerous cell.

Typically, said vector can be a viral vector. Oncoretroviral and lentiviral vectors exhibit promising features because they have the ability to produce stable transduction, maintain long-term transgene expression and, for lentiviruses, enable transduction of non-dividing cells.

Alternatively, said vector is an adeno associated virus (AAV) vector. AAV is a replication-deficient parvovirus, the single-stranded DNA genome of which is about 4.7 kb in length including 145 nucleotide inverted terminal repeat (ITRs). AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible.

Multiple serotypes of AAV exist and offer varied tissue tropism. Known serotypes include, for example, AAV1, AAV2, AAV3, AAV4, AAV5, AAV6, AAV7, AAV8, AAV9, AAV10 and AAV11.

Preferably, said vector is an adeno associated virus vector, preferably a recombinant adeno associated virus vector.

More preferably, in the context of the invention, said vector is AAV9. The use of adeno-associated virus 9 is highly convenient for delivering a gene in a brain cell, since AAV9 is able to cross the blood brain barrier.

Therefore, in a preferred embodiment, the invention relates to a vector encoding ApoO for treating glioblastoma, by inducing lipotoxicity, mitochondrial dysfunction and eventually apoptosis of glioblastoma cells, wherein said vector is a adeno-associated virus 9 that expresses ApoO.

As used herein, the expression "biological function and/or activity of native ApoO" refers to the ability of ApoO to interact with CypD and ANT, driving the MPTP to adopt an open state and/or increases mitochondrial respiration, increases fatty acid metabolism and induces lipid accumulation.

The skilled person is aware of the most appropriate route of administration. Preferably, the compound of the invention may be administered orally, sublingually, subcutaneously, intramuscularly, intravenously, transdermally, locally. Most preferably, the compound of the invention is administered by injection, e.g. by intra-arterial, intra-peritoneal or preferably intravenous injection in a dosage which is sufficient to obtain the desired pharmacological effect.

The attending physician would know how to and when to terminate, interrupt, or adjust administration. Conversely, the attending physician would also know to adjust treatment to higher levels if the clinical response were not adequate. The magnitude of an administered dose in the management of the disorder of interest will vary with the severity of the condition to be treated. The severity of the condition may, for example, be evaluated, in part, by standard prognostic evaluation methods. Further, the dose and perhaps dose frequency, will also vary according to the age, body weight, and response of the individual patient. A program comparable to that discussed above may be employed in veterinary medicine.

Treatment of Pathologies Attributed to Excess Lipid Accumulation

By experimenting on human hearts, murine livers and cardiac myoblasts, the inventors found out that overexpression of ApoO was associated with a high level of apoptosis, which was evidenced, inter glia, by high caspase-3 activity. Therefore, they have put in light, for the very first time, that overexpression of ApoO increases apoptosis rate.

Inhibition of ApoO was thus found to be highly appropriate for treating and/or preventing a disorder associated with obesity such as nonalcoholoc fatty liver disease, type 2 diabetes and lipotoxic cardiomyopathy. Indeed, those pathologies are attributed to excess lipid accumulation in organs, leading to lipotoxicity which is responsible for apoptosis. The administration of an inhibitor of the ApoO activity or of an ApoO gene expression therefore minimizes the lipotoxicity, leading to an enhanced rate of survival of the target cells. The inventors met the burden to show that lipotoxicity is a consequence and not a cause of mitochondrial dysfunction.

Therefore, in a second aspect, the invention relates to a compound for use in a method for treating a pathophysiological situation selected from the group consisting of obesity, diabetes, fatty liver, pancreatitis, and hypothyroidism, wherein said compound is an inhibitor of the ApoO activity or of the ApoO gene expression. Preferably, said pathophysiological situation is selected from the group consisting of obesity, and diabetes.

In a specific embodiment, said compound is used in a method for reducing lipid overload in a pathophysiological situation, preferably in obesity, diabetes, cardiomyopathy, myopathy, fatty liver, pancreatitis, and/or hypothyroidism, wherein said compound is an inhibitor of the ApoO activity or of the ApoO gene expression. Preferably, said pathophysiological situation is selected from the group consisting of obesity, diabetes and cardiomyopathy.

Preferably, said subject suffers from diabetes and/or obesity.

The expression "inhibitor of the ApoO activity or of the ApoO gene expression" should be understood broadly, the expression refers to agents downregulating the expression of ApoO or compounds that bind to ApoO.

An "inhibitor of expression" refers to a natural or synthetic compound that has a biological effect to inhibit or significantly reduce the expression of a gene. Consequently an "inhibitor of the ApoO gene expression" refers to a natural or synthetic compound that has a biological effect to inhibit or significantly reduce the expression of the gene encoding for the ApoO protein.

As used herein, the term "ApoO activity" denotes the capacity of the ApoO to bind to lipids to transport through the lymphatic and circulatory systems or to enhance lipid uptake and lipid metabolism within cells.

In one embodiment, the compound according to the invention may be a low molecular weight inhibitor, e. g. a small organic molecule (natural or not).

The term "small organic molecule" refers to a molecule (natural or not) of a size comparable to those organic molecules generally used in pharmaceuticals. The term excludes biological macromolecules (e. g., proteins, nucleic acids, etc.). Preferred small organic molecules range in size up to about 5000 Da, more preferably up to 2000 Da, and most preferably up to about 1000 Da.

In another embodiment, the compound according to the invention is an antibody which binds to the ApoO protein and inhibits the ApoO activity.

Antibodies directed against the ApoO protein can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against the ApoO protein can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see, e.g., U.S. Pat. No. 4,946,778) can be adapted to produce anti-ApoO single chain antibodies. ApoO inhibitors useful in practicing the present invention also include anti-ApoO antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to the ApoO.

Humanized anti-ApoO antibodies and antibody fragments thereof may also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

In still another embodiment, ApoO inhibitor may be selected from aptamers. Aptamers are a class of molecules that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consist of conformationally constrained antibody variable regions displayed by a platform protein, such as *E. coli* Thioredoxin A that are selected from combinatorial libraries by two hybrid methods (Colas et al., 1996). Moreover, aptamers can be coupled to membrane-permeant targeting peptide-based method that rapidly and reversibly knocks down endogenous proteins through chaperone-mediated autophagy in vitro and in vivo (Fan X, Nature Neuroscience 2014).

In another embodiment, small inhibitory RNAs (siRNAs) can also function as inhibitors of ApoO gene expression for use in the present invention. ApoO gene expression can be reduced by contacting a subject or cell with a small double stranded RNA (dsRNA), or a vector or construct causing the production of a small double stranded RNA, such that ApoO gene expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of ApoO gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of ApoO mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of ApoO gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing ApoO. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and Rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, eye, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide, siRNA, shRNA or ribozyme nucleic acid sequence is under the control of a heterologous regulatory region, e.g., a heterologous promoter. The promoter may be specific for Muller glial cells, microglia cells, endothelial cells, pericyte cells and astrocytes. For example, a specific expression in Muller glial cells may be obtained through the promoter of the glutamine synthetase gene. The promoter can also be, e.g., a viral promoter, such as CMV promoter or any synthetic promoters.

In a preferred embodiment, the compound according to the invention is a shRNA. Said shRNA acts as an inhibitor of ApoO activity or an inhibitor of the ApoO gene expression. Preferably, said shRNA are from MISSION shRNA set and are selected from sh4 (TRCN 72707) and Sh5 (TRCN 72705), marketed by Sigma Aldrich, Saint Quentin Fallavier.

Therapeutic Composition

Another object of the invention relates to a therapeutic composition comprising a compound for the treatment of a cancer, more preferably for inducing apoptosis in a cancerous cell wherein said compound is selected from the group consisting of ApoO, a variant or a fragment thereof, and their mixtures.

Another object of the invention also relates a therapeutic composition comprising a compound for treating and/or preventing a pathophysiological situation selected from the group consisting of obesity, diabetes, fatty liver, pancreatitis, and hypothyroidism, wherein said compound is an inhibitor of the ApoO activity or of the ApoO gene expression.

The person skilled in the art would be aware of the effective amount of ApoO, a variant or a fragment thereof, their mixtures or a vector encoding said ApoO, variant or fragment thereof to administrate for fulfilling the desired aim.

By an "effective amount of ApoO, a fragment or a derivative thereof, their mixtures or a vector encoding said ApoO, variant or fragment thereof" is meant a sufficient amount to induce apoptosis of a cancerous cell or reduce lipid overload in a pathophysiological situation, at a reasonable benefit/risk ratio applicable to any medical treatment. It will be understood, however, that the total daily usage of ApoO, a fragment or a derivative thereof, their mixtures or a vector encoding said ApoO, variant or fragment thereof will be decided by attending physician within the scope of sound medical judgment. The specific therapeutically effective dose level for any particular subject in need thereof will depend upon a variety of factors including the stage of the disorders being treated and the activity of the specific ApoO, the fragment or the derivative thereof or the vector comprising a nucleic acid coding for ApoO employed, the age, body weight, general health, sex and diet of the subject, the time of administration, route of administration, the duration of the treatment, drugs used in combination or coincidental with the treatment.

Any therapeutic agent of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

In addition, other pharmaceutically acceptable forms include, e.g. tablets or other solids for oral administration, time release capsules, and any other form currently can be used.

The invention will be further illustrated by the following figures and examples. However, these examples and figures should not be interpreted in any way as limiting the scope of the present invention.

FIGURES

FIG. 1: ApoO and ApoO Δ1-40 expression and localization in cardiac myoblasts.

(a) ApoO mRNA levels in control cardiac myoblasts and transfectants stably overexpressing ApoO. SH2, SH3, SH4 and SH5 indicate 4 independent ApoO clones subsequently stably transfected with 4 different shRNA-ApoO expression vectors;

(b) ApoO Western blot analysis with total protein extracts prepared from control, ApoO and shRNA-ApoO cells;

(c) Equal lane loading and transfer were verified by probing the same membrane with calreticulin antibody;

(d) Quantification of the ApoO to calreticulin signal;

(e) Western blot for ApoO with membrane protein extracts prepared from ApoO and control cells. Equal lane loading and transfer were verified by probing the same membrane with calreticulin antibody;

Western blot analysis of cytoplasmic and mitochondrial fractions of cardiac myoblasts overexpressing (f) ApoO or (g) ApoOΔ1-40 hybridized with ApoO Ab.

Actin and ANT were used as cytosolic and mitochondrial purification controls, respectively. Representative data from one experiment is shown. Experiments were repeated three times. Labels are: Mitochondria (Mit), cytoplasm (Cyto.). **$p<0.01$.

Figure 2:
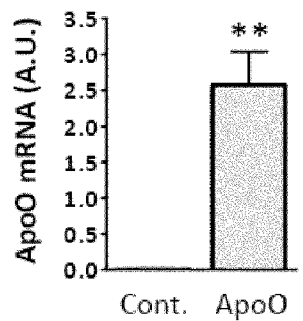

FIG. 2: hApoO expression in in vivo transfected liver.

Human ApoO mRNA levels in mouse liver after hydrodynamics-based in vivo liver transfection by rapid tail vein injection of control (n=12) and ApoO (n=12) expression vectors. **$p<0.01$.

Figure 3:
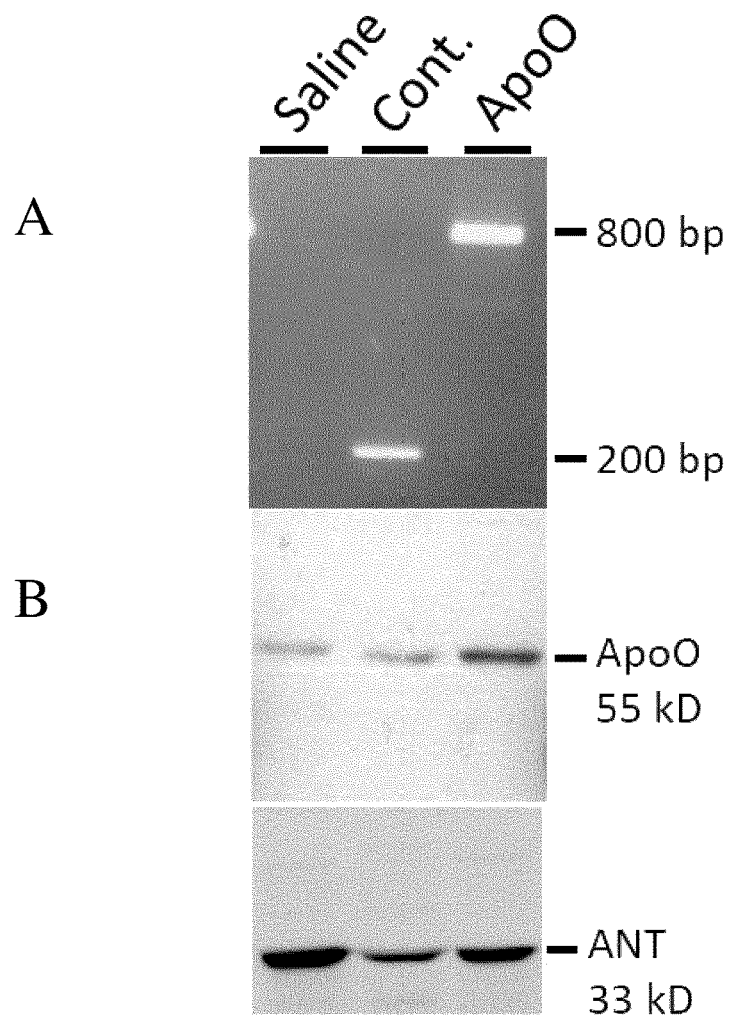

FIG. 3: ApoO is mitochondrial.

(A) 2% ethidium bromide stained agarose gel electrophoresis of PCR amplified products obtained from mouse liver after hydrodynamics-based in vivo liver transfection by rapid tail vein injection of control (n=12), hApoO expression vector (n=12), and saline (n=12).

(B) Western blot of protein extracts from isolated liver mitochondria probed with ApoO antibody shown above the loading/transfer control performed by probing the transferred membrane with ANT antibody.

Figure 4:
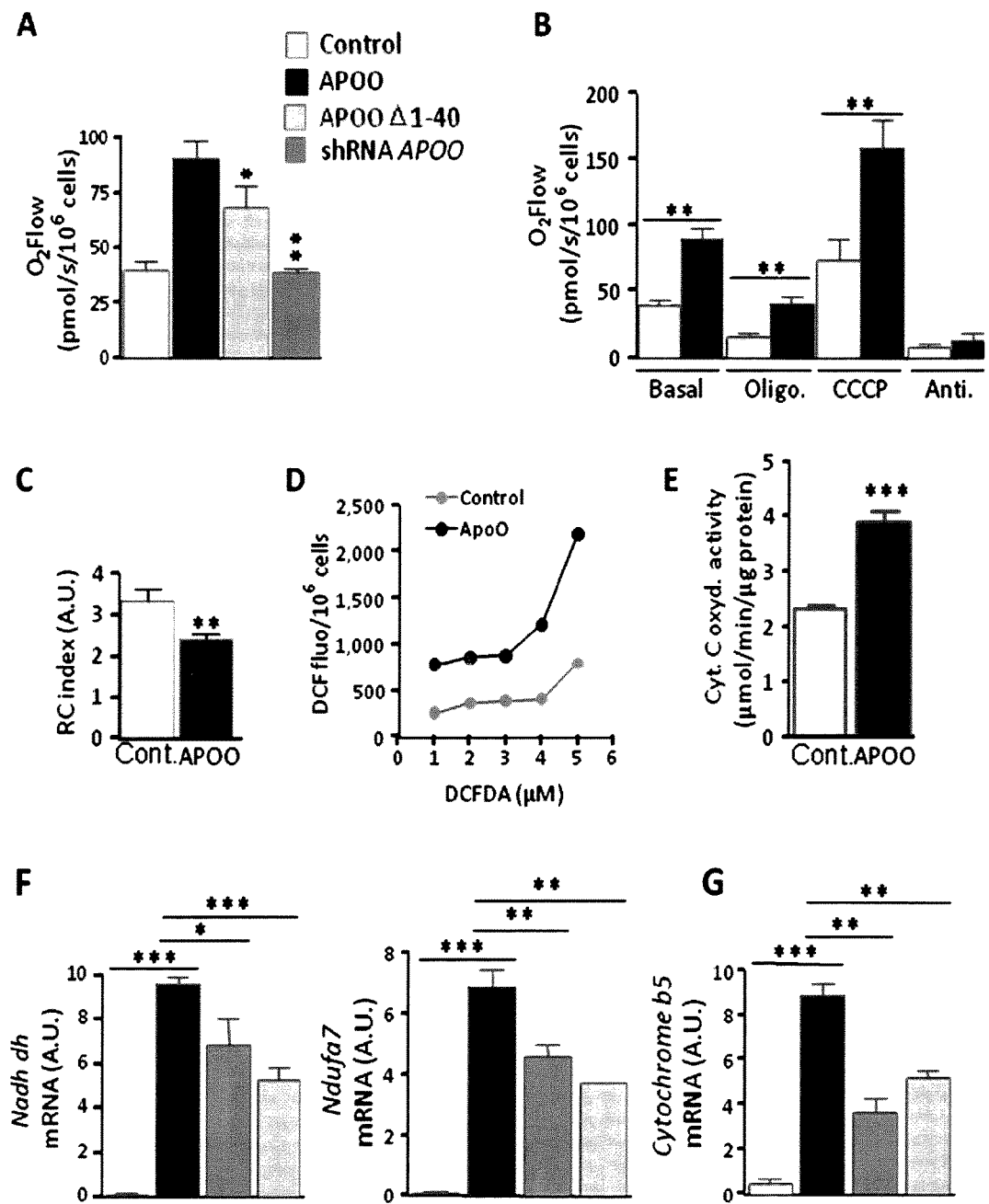

FIG. 4: Role of ApoO in respiration and oxidative stress in cardiac myoblasts.

(a) Basal oxygen consumption in control cells, stable transfectants expressing ApoO, ApoOΔ1-40 or ApoO treated with shRNAApoO (n=5).

(b) Oxygen consumption of control and ApoO cells treated with different drugs: 1.5 μg/ml oligomycin (Oligo), 2 μM carbonyl cyanide m-chlorophenyl hydrazone (CCCP), and 1 μM antimycin (Anti.) (n=5).

(c) The respiration control index (RC) in control and ApoO cells.

(d) Reactive oxygen species measured in the presence of increasing doses (1-6 μM) of 2',7' dichlorodihydrofluorescein diacetate (DCFDA) in control and ApoO cells (n=4).

(e) Cytochrome C oxidase activity in control and ApoO cells (n=4).

(f) Geneexpression levels of mitochondrial complex I and (g) complex III in control, ApoO, shRNAApoO and ApoOΔ1-40 cells. (n=5). A.U.: Arbitrary units. *$p<0.05$, $p<0.01$, *$p<0.001$. Data represent mean±SEM.

Figure 5:
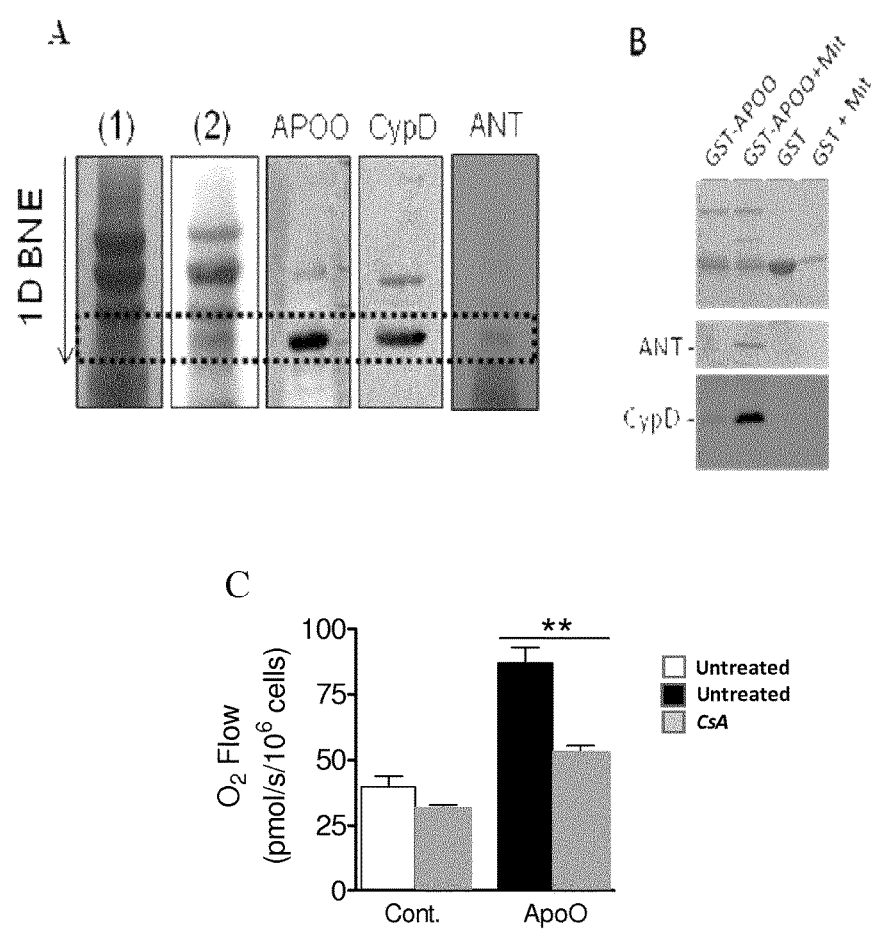

FIG. 5: ApoO interacts with ANT and CyPD in the mitochondrion.

(A) One-dimensional BN-PAGE gel analysis of mitochondrial protein complexes from mouse heart. (1): Coomassie blue staining of the 4-13% polyacrylamide one-dimensional gradient blue native gel. (2): Ponceau S staining of the transferred PVDF membrane. ApoO, ANT and CypD were detected using enhanced chemiluminescence of the transferred PVDF membranes with ApoO, ANT or CypD antibodies respectively. ApoO, ANT and CypD were detected in the same complex (black rectangle).

(B) Western blot analysis of ApoO-GST pull-down. Upper panel: Ponceau S staining of the transferred membrane used to control loading and transfer. Lower panels: ANT and CypD detection using enhanced chemiluminescence of the same membrane probed with ANT or CypD antibodies, labels are: GST-ApoO fusion protein incubated without (GST-ApoO) or with (GST-ApoO+Mit) heart mitochondria protein extracts, GST alone (GST) or with heart mitochondrial protein extracts (GST+Mit).

(C) CypD inactivation reduces ApoO-induced respiration: Oxygen flow in control cardiac myoblasts and cardiac myoblasts overexpressing ApoO treated 50 min with or without 200 nM cyclosporine A (CsA) (n=5).

Figure 6:
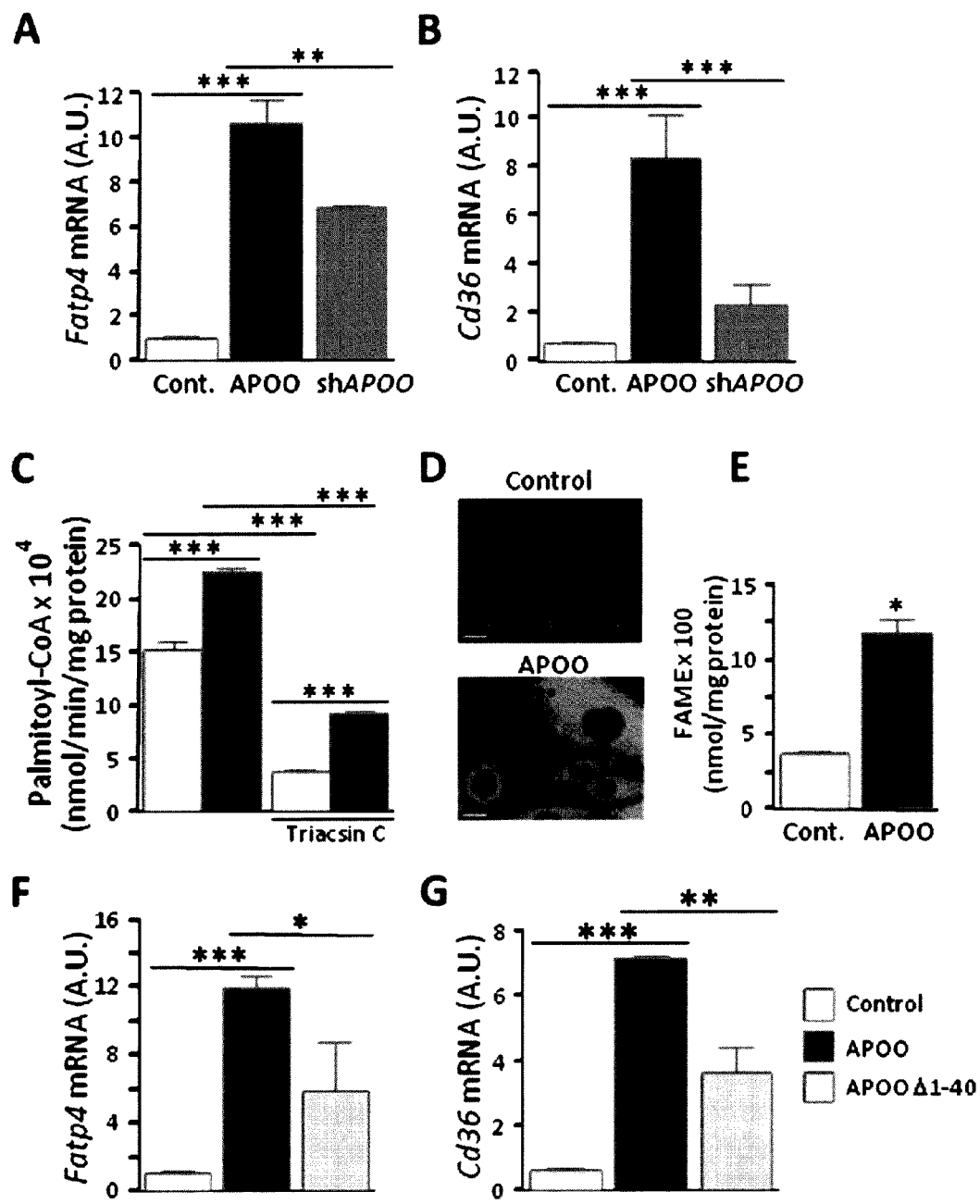

FIG. 6: ApoO induces fatty acid metabolism in cardiac myoblasts.

(A) Fatp4 and (B) Cd36 mRNA expression levels in control cells, ApoO cells and ApoO cells where ApoO was subsequently knocked-down with shRNA ApoO (shApoO) (n=5).

(C) Palmitoyl-CoA synthesis rate in control and ApoO cells with and without 5 μM triacsin C, an ACSL inhibitor (n=5).

(D) Confocal microscopy images of control and ApoO cells incubated 2 minutes with BODIPY-palmitate, a fluorescent analog of palmitate, scale bar=10 μm.

(E) Intracellular levels of total fatty acids (indicated as FAME or fatty acid methyl ester) in control and ApoO expressing cells (n=6).

(F) Fatp4 and (G) Cd36 mRNA levels in control, ApoO or ApoOΔ1-40 cells. *$p<0.05$, **$p<0.01$, $p<0.001$. Data represent mean±SEM.

Figure 7:
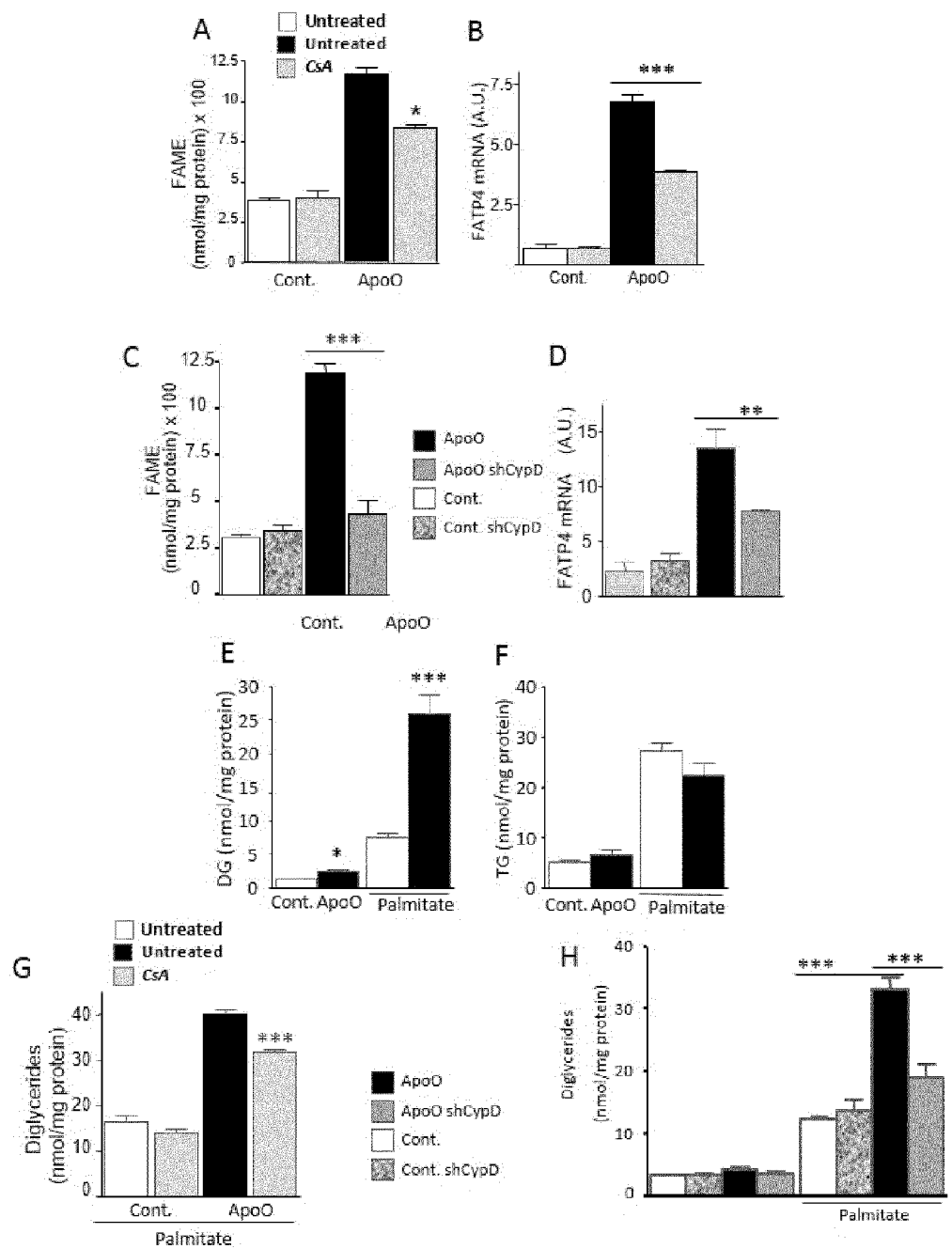

FIG. 7: Cyclophilin D knock-down reduces ApoO-induced lipotoxicity in cardiac myoblasts:

(A), (B) Total fatty acid and FATP4 mRNA levels in control and ApoO cells with and without a 8 hour treatment of 20 nM CsA (n=5).

(C) Intracellular levels of FAME in control cells (Cont.) and ApoO cells with and without subsequent transfection with an shRNA-Cyclophilin D expression vector (Cont.-shCypD and ApoO-shCypD). (D) RT-qPCR analysis of FATP4 mRNA levels in these cells.

(E), (F) Intracellular levels of diglycerides (DG) and triglycerides (TG) in control and ApoO cells with or without 8 hour incubation of 100 μM palmitate (n=5).

(G), (H) Diglyceride levels in control and ApoO cells with or without a 8 hour incubation of 100 μM palmitate and 20 nM Cyclosporine A (CsA) (n=5).

Diglycerides levels in control, ApoO, Cont.-shCypD and ApoO-shCypD cells. (n=4). *p<0.05, p<0.01, *p<0.001.

Figure 8:
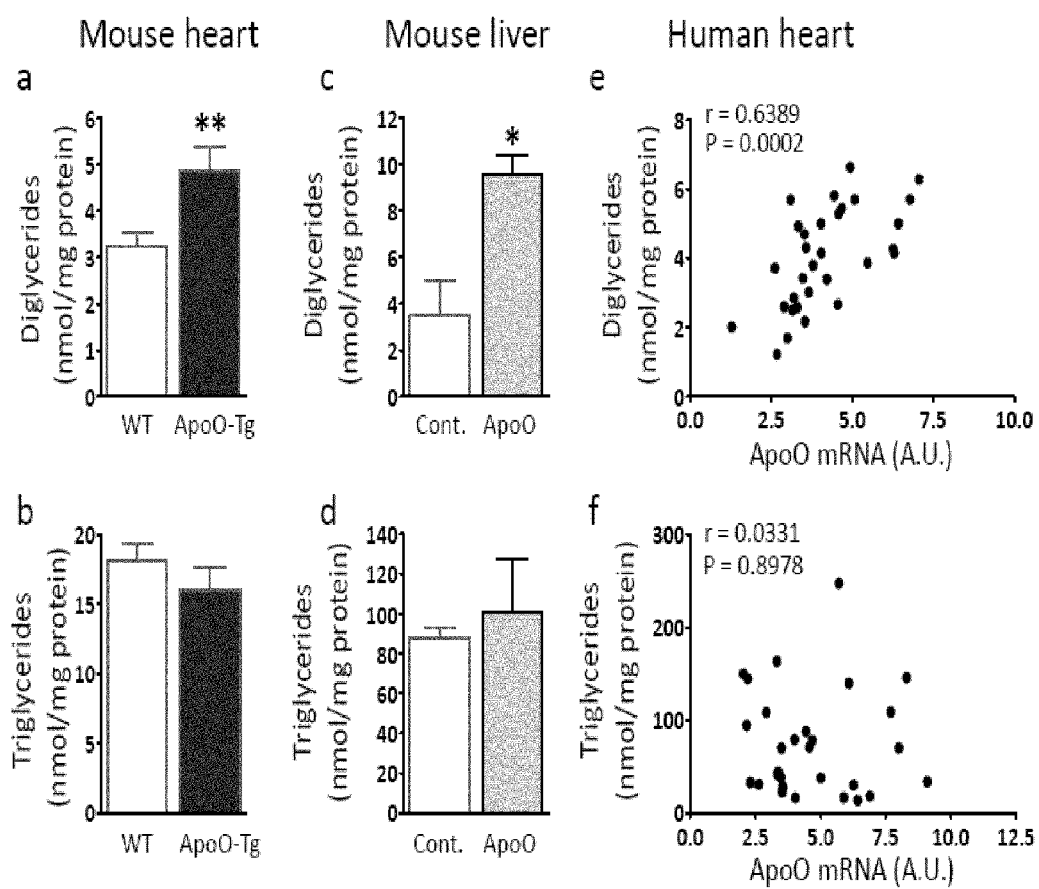

FIG. 8: ApoO enhances intracellular levels of lipotoxic byproducts in mouse and human heart.

(a), (b) Diglyceride and triglyceride levels in wild type (WT, n=12) and cardiac-specific ApoO transgenic mouse hearts (ApoO-Tg, n=11).

(c), (d) Diglyceride and triglyceride levels in the liver after hydrodynamics-based in vivo transfection by a rapid tail vein injection of control (n=12) and ApoO (n=12) expression vectors.

(e), (f) Correlation between ApoO mRNA level and the intracellular concentration of diglycerides (n=30) or triglycerides (n=27) in human atrial heart appendage samples. *p<0.05, **p<0.01.

Figure 9:
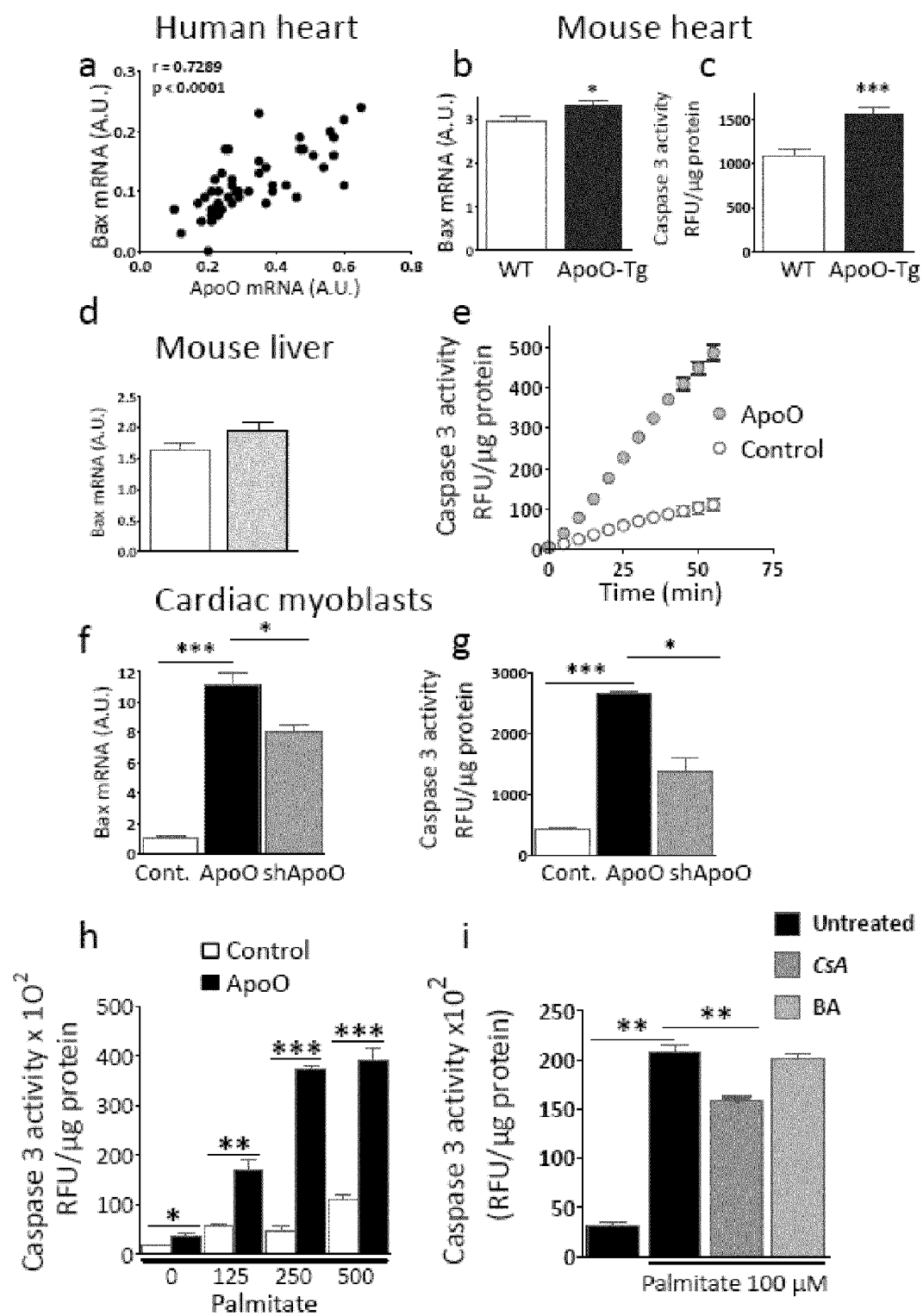

FIG. 9: ApoO induces apoptosis in vivo and in vitro.

(a) Positive correlation between ApoO and Bax mRNA levels in human atrial appendage samples (n=48).

(b), (c) Bax mRNA levels and Caspase-3 activity in wild type (WT, n=15) and cardiac specific transgenic mice (ApoO-Tg, n=16).

(d), (e) Bax mRNA levels and Caspase-3 activity in liver 48 hours after hydrodynamics-based in vivo liver transfection by rapid tail vein injection of control and ApoO expression vectors (n=12).

(f), (g) Bax mRNA levels and Caspase-3 activity in control cells, ApoO cells, and ApoO cells subsequently stably transfected with shRNA-ApoO expression vector (shApoO).

(h) Caspase-3 activity in control and ApoO expressing cells incubated overnight with increasing concentrations of palmitate (n=6).

(i) Caspase-3 activity from H9c2 cardiac myoblasts stably expressing ApoO with or without 12 hour incubation of 100 μM palmitate and either 20 nM cyclosporine A (CsA), or 30 μM Bonkretic acid (BA) (n=4). *p<0.05, p<0.01, *p<0.001.

Figure 10:
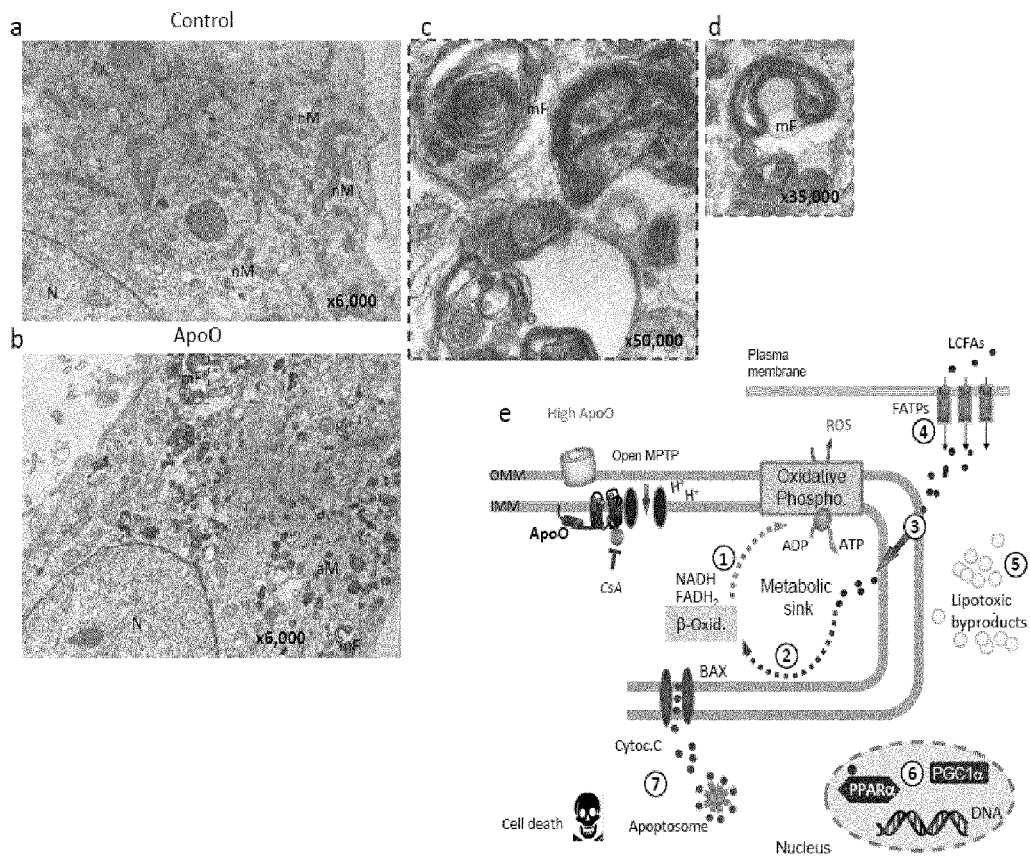

FIG. 10: Mitochondrial alteration and degradation in cardiac myoblasts overexpressing ApoO.

(a), (b) Transmission electron microscopy analysis of control and ApoO cells treated for 24 hours with 100 μM palmitate.

(c), (d) Degradation of mitochondria in autophagosomal vacuoles and multilamellar bodies (myelin figure, mf) in ApoO cells. Normal mitochondrion (nM) and the nucleus (N) are labeled.

(e) Schematic illustration depicting the role of ApoO. (1) ApoO-induced mild uncoupling activates the electron transport chain, which requires more NADH/FADH$_2$. (2) In adult heart, NADH and FADH$_2$ production is mainly generated by β-oxidation of long chain fatty acids (LCFAs) and their consumption generates a mitochondrial metabolic sink. (3) LCFAs enter rapidly into the mitochondria through CPT-1 and the open MPTP. (4) Increased expression of LCFA transporters (FATPs) compensate for the increased mitochondrial consumption. (5) LCFA uptake exceeds mitochondrial fatty acid oxidative capacity and leads to lipotoxicity. (6) The enhanced oxidative stress and mitochondrial dysfunction increases the expression of genes involved in lipid uptake, β-oxidation, and mitochondrial biogenesis (such as PGC1α and PPARα). (7) Increased ROS levels further stimulate MPTP opening and proton gradient loss, which act together with Bax to release apoptosis inducing factor (AIF) and cytochrome C, leading to cell death. The Outer (OMM) and inner (IMM) mitochondrial membrane are labeled.

Figure 11:
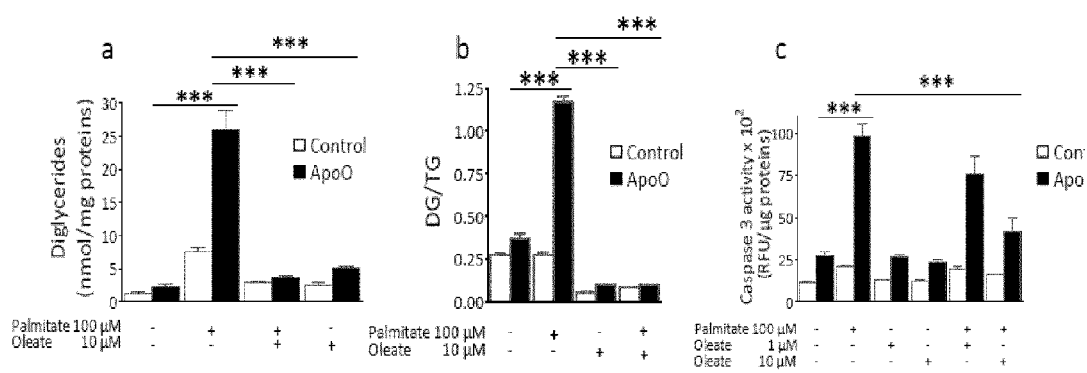

FIG. 11: ApoO increases diglyceride levels in cardiac myoblasts.

(a) Intracellular levels of diglycerides in H9c2 cardiac myoblasts stably transfected with control (n=4) and ApoO expression vectors (n=4) with or without 12 hours incubation with 100 μM palmitate and 10 μM oleate.

(b) Intracellular diglyceride (DG) to triglyceride (TG) ratios in H9c2 cardiac myoblasts stably transfected with control (n=4) and ApoO expression vectors (n=4) with or without 12 hours incubation with 100 μM palmitate and 10 μM oleate. (c) Caspase-3 activity from H9c2 cardiac myoblasts stably transfected with control (n=6) and ApoO expression vectors (n=6) with or without 12 hours incubation with 100 μM palmitate and either 1 or 10 μM oleate. p<0.01, *p<0.001

Figure 12:
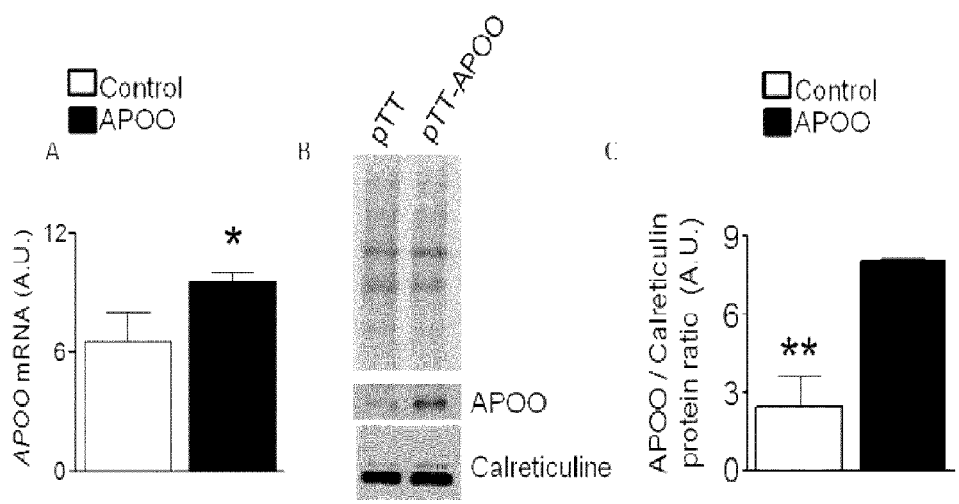

FIG. 12: U87 transfectants overexpression ApoO (A) Human ApoO mRNA levels in U87 control cells transfected with the empty vector (pTT) and transfectants stably overexpressing ApoO (pTT-ApoO).

(B) ApoO Western blot analysis with total protein extracts prepared from control and ApoO cells.

Equal lane loading and transfer were verified by probing the same membrane with calreticulin antibody.

(C) ImageJ quantification of the ApoO to calreticulin signal. Representative data from one experiment is shown. Experiments were repeated three times. *p<0.05.

Figure 13:
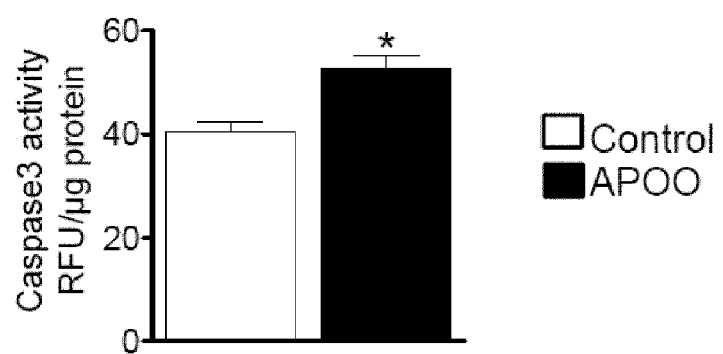

FIG. 13: ApoO induces apoptosis in U87 cells

Caspase-3 activity in control and ApoO expressing cells incubated overnight with 100 μM palmitate (n=4). *p<0.05. Data represent mean±SEM.

Figure 14:
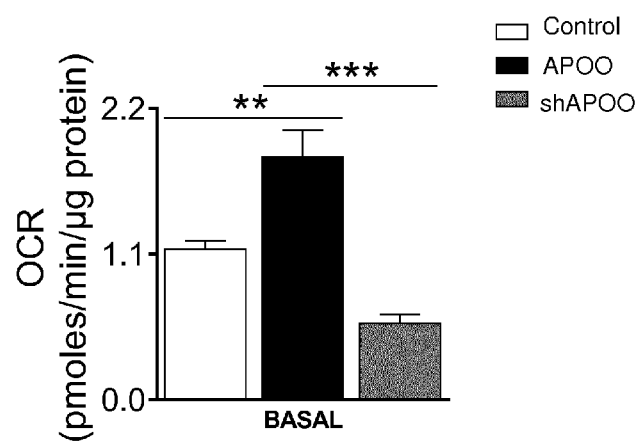

FIG. 14: Overexpression of ApoO enhances cancer cells respiration.

Basal oxygen consumption rate (OCR) in control cells, ApoO expressing cells (ApoO cells) and ApoO cells subsequently transfected with shApoO (n=3).P<0.01, *P<0.001. Data represent mean±SEM.

Figure 15:
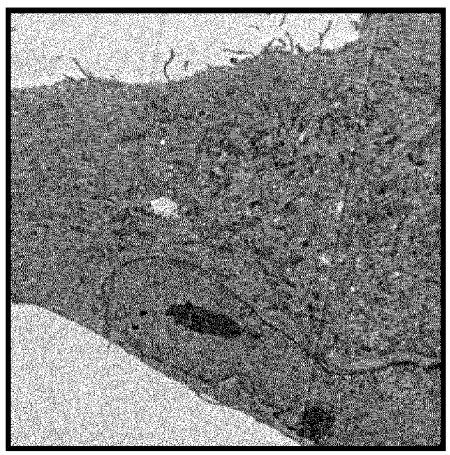
Figure 15:
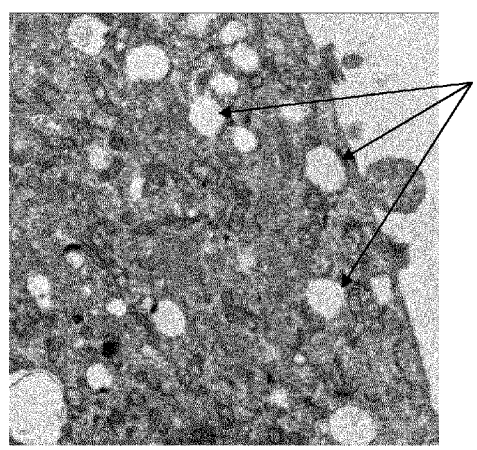

FIG. 15: Overexpression of ApoO promotes lipotoxicity in cancer cells.

Transmission electron microscopy of control (left) and ApoO expressing (right) cells incubated overnight with 100 μM of palmitate (n=6). Black arrows indicate lipid droplets.

Figure 16:
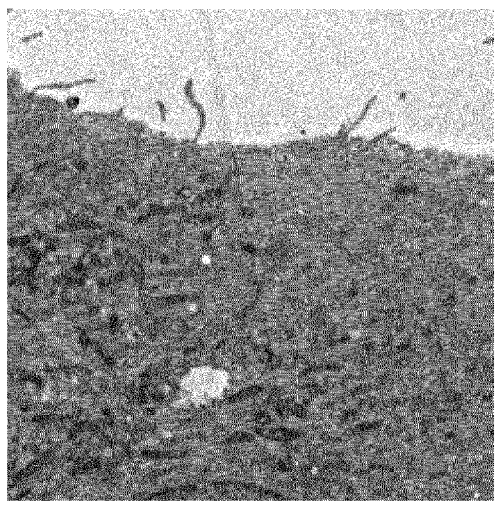
Figure 16:
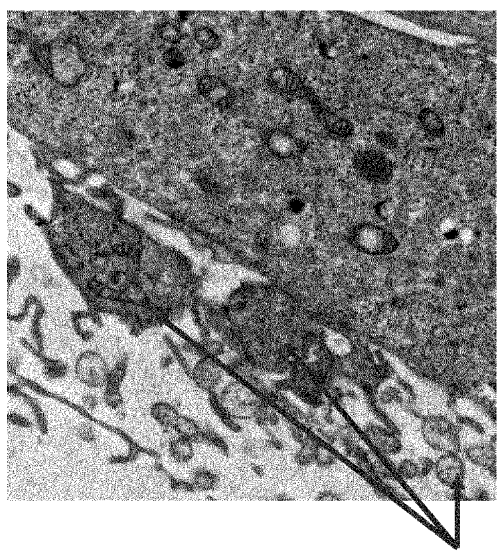

FIG. 16: Overexpression of ApoO promotes membrane blebbing in cancer cells.

Transmission electron microscopy of control (left) and ApoO expressing (right) cells. Black arrows indicate blebs (n=3).

EXAMPLES

Example 1: Linking Mitochondrial Dysfunction to Lipotoxicity with ApoO

Apolipoproteins (Apos) were first characterized to bind lipoproteins that facilitate the plasma lipid transport process through the lymphatic and circulatory systems. However, different unexpected functions have also been identified for Apos. ApoE activates Akt/PKB phosphorylation, ApoJ can be translocated to the nucleus where it binds to the DNA repair protein Ku80. Finally, ApoL6, which has structural homologies with Bcl2 family members, regulates pathways such as autophagy.

Through a functional genomics study aimed at identifying genes differentially regulated in the heart by obesity, the inventors discovered a new apolipoprotein (ApoO) that is overexpressed in hearts from diabetic patients. In order to uncover how changes in the expression of this protein relate to modifications of cardiac function, they performed in vitro and in vivo manipulations utilizing cardiac myoblasts, three independent cardiac specific transgenic mouse lines expressing ApoO at physiological levels, in vivo transfected mouse liver and human heart samples. The inventors first show that ApoO localizes to mitochondria and interacts with cyclophilin D and adenine nucleotide translocase (ANT) causing the mitochondrial permeability transition pore (MPTP) to adopt an open state, inducing mild uncoupling. MPTP was first considered to play a key role in the "life or death" decision of the cell and was proposed as a target for cardio protection during heart disease. This pore enables free passage of metabolites and molecules of molecular mass below 1.5 kDa into the mitochondria including protons, which leads to uncoupling. The exact protein composition of MPTP is still under debate but minimally includes cyclophilin D and ANT, which is proposed to serve as a regulatory component.

Reduced cardiac efficiency is one of the hallmarks of obesity and Type 2 diabetes in both rodents and humans. The mechanism for increased myocardial V o2 and decreased cardiac efficiency are incompletely understood. Increased mitochondrial uncoupling was suggested to be one of the underlying mechanism that affects cardiomyocyte energetics and contractility, contributing to the growing epidemic of diabetic cardiomyopathy. Thus, MPTP regulators are of central importance to control mitochondrial dysfunction and the fate of cardiomyocytes.

Materials and Method
Human Heart Samples.

After ethical committee approval, all patients in this study gave written consent for sample collection and molecular analysis prior to inclusion. Patients were carefully selected by physicians from the Department of Cardiology, Toulouse University Hospital, prior to coronary by-pass surgery.

Bioinformatics.

Microarray expression data from human heart samples were downloaded from the GEO repository (GSE1145). This series consisted of 107 myocardial samples collected from patients undergoing cardiac transplantation whose failure arises from different etiologies (e.g. idiopathic dilated cardiomyopathy, ischemic cardiomyopathy, valvular cardiomyopathy, and hypertrophic cardiomyopathy) and from "normal" organ donors whose hearts cannot be used for transplants. Arrays were intensity normalized and hierarchical clustering (average group linkage, Pearson correlation, threshold r=0.8) was applied to identify groups of co-expressed genes. ApoO expression levels were plotted for the 107 human hearts tested and used to define relevant molecular pathways using both Toppgene and Ingenuity Pathway Analysis (Ingenuity systems, Redwood City, Calif., USA). ApoO subcellular localization was predicted using Mitopred, mitoprot and YLoc.

Animals:

All animal Studies followed the INSERM Institute Animal Facility guidelines and were approved by the animal care committees of the INSERM I2MC UMR 1048. All animal procedures were performed according to the guidelines of the French Ministry of Agriculture. Animals were housed at the Toulouse I2MC animal facility in a room lit 12 h per day (6 AM-6 PM) at an ambient temperature of 22+/−1° C.

Construction of ApoO Expression Vectors

To overexpress human ApoO (pTT-ApoO), the ApoO coding sequence was amplified using primers hApoO5BamPTT (SEQ ID NO: 2) and hApoO3BamPTT (SEQ ID NO: 3) and cloned into the BamH1 site of pTT expression vector. pSNAP-ApoO was generated by PCR amplification of pTT-ApoO using primers SnapApoEcorV-F (SEQ ID NO: 4) and SnapApoEcorV-R (SEQ ID NO: 5) and cloned into the EcoRV site of pSNAP-Tag® (Ozyme, Saint-Quentin-en-Yvelines, France). pGEX2T-ApoO was constructed by PCR amplification of pTT-ApoO using hApoOpGEX1FBam (SEQ ID NO: 6) and hApoOpGEX1RSma (SEQ ID NO: 7) and cloned into the Bam HI/Sma I site of pGEX2T (Promega, Charbonnières-les-Bains). All primers used in this work were synthesized by Eurogentec France (Angers). All restriction enzymes used were from New England Biolabs (Ozyme, Saint-Quentin-en-Yvelines). All ApoO sequences within the expression vectors were verified by DNA double strand sequencing using ABI PRISM®BigDye™ Terminator version 3.1 Ready reaction cycle sequencing kit (Life Technologies SAS, Villebon sur Yvette) and loaded on an ABI 3130XL DNA sequencing instrument (Life Technologies SAS, Villebon sur Yvette).

Cell Culture and Tranfection of H9C2 Cardic Myoblasts

H9c2 were obtained from the European Collection of Cell Cultures (Salisbury, England). H9c2 cells were cultured in Dulbecco's modified Eagle medium (Life Technologies SAS, Villebon sur Yvette) adjusted to contain 1.5 g/liter sodium bicarbonate and supplemented with antibiotic-antimycotic solution (Life Technologies SAS, Villebon sur Yvette) and 10% fetal bovine serum (FBS, AbCys s.a., Paris). Cells were plated on 10-cm diameter tissue culture dish and grown in a 5% $CO_2$ incubator at 37° C. with saturating humidity with medium changes every 2 days. H9c2 cardiomyoblasts were stably transfected by electroporation and pools of tranfectants were selected as previously published.

Knock-Down of ApoO Overexpression shRNA used to knock-down ApoO gene expression and controls were from MISSION shRNA set; Sh2=TRCN 72707; Sh4=TRCN 72704; Sh5=TRCN 72705 (Sigma Aldrich, Saint-Quentin Fallavier) and used as recommended by generating pools of stable transfectants. Empty vector (no shRNA insert) control was also transfected and had no significant effect.

Membrane Preparations

Membrane preparation were performed as described in Harmancey, R. et al, western diet changes cardiac acyl-CoA composition in obese rats: a potential role for hepatic lipogenesis. *J Lipid Res* 51, 1380-1393, (2010).

Functional Genomics

Total RNA were purified using RNeasy kit (Qiagen, Courtaboeuf) in a Qiacube (Qiagen, Courtaboeuf) automated protocol. Total RNA integrity was checked by Experion capillary electrophoresis (Bio-Rad, Marnes La Coquette). Samples with RNA Quality Indicator ≥8.5/10 were selected for analyses. Total RNAs were precisely quantified using RiboGreen and a Victor™ X5 2030 multilabel reader (Perkin Elmer, Courtaboeuf). Total RNA was used for fluorescent labelling with ChipShot™ Direct Labeling kit (Promega, Charbonnieres-les-Bains). Labeled RNA was hybridized to pangenomic rat glass microarrays. After standard hybridization, glass arrays were washed on a Ventana Discovery hybridization and wash system (Ventana Medical Systems SA, Illkirch) and scanned using a GenPix 4000 scanner (Molecular Devices France, St. Grégoire). Scanned images were processed by X-dot reader software (COSE, Paris) with operator's validation of the spots detection. Microarray data were analyzed using both Toppgene and Ingenuity pathway analysis software (Ingenuity systems, Redwood City, Calif., USA).

Palmitate Preparation and Caspase 3 Activity Monitoring
Palmitate preparation and Caspase-3 activity measurements were performed as described in Hickson-Bick et al, *J Mol Cell Cardiol* 32, 511-519, (2000) and Hirota, et al. *Life Sci*79, 1312-1316, (2006).

Echocardiographic Analysis
Echocardiograms were performed by using the Vivid 7 PRO echocardiographic system (GE Medical System, Velizy), equipped with a i13 L 14-MHz linear-array transducer. Images were obtained from chest-shaven rats lightly anesthetized by 1-2% isoflurane (Baxter, Maurepas) lying on their back side with transducers placed on the left hemithorax. Two-dimensional parasternal long- and short-axis images of the left ventricle were obtained and two-dimensional targeted M-mode tracings were recorded at a sweep speed of 200 mm/s. All measurements were performed according to the recommendations of the American Society for Echocardiography. The leading-edge method was applied to three consecutive cardiac cycles (n) with the roundness of the left ventricular cavity (2D-image) as a criterion that the image was on axis. Great effort was taken to achieve a good image quality and to visualize the endocardial and epicardial borders of the heart by gently moving and angulating the transducer. Percent left ventricular (LV) fractional shortening (FS), a measure of LV systolic function, was calculated by the formula FS=(EDD−ESD)/EDD× 100, where EDD and ESD are end-diastolic and end-systolic diameters, respectively.

Electrocardiogram
Surface electrocardiograms (ECGs) were recorded using an ADI system (ADinstruments LTD, Oxford, UK).

Generation of Cardiac Specific Human ApoO Transgenic Mice
Studies on transgenic mice were carried out in agreement with French laws and INSERM guidelines on animal care. The α myosin heavy chain (αMHC)-ApoO transgene was constructed from a 5.5 kb BamHI-SalI fragment containing the murine αMHC promoter and a SalI-Hind III cDNA fragment containing the human ApoO coding sequence. The αMHC-ApoO transgene was linearized with NotI, purified by electroelution, concentrated on an elutip-d column (Schleicher and Schuell), and used for nuclear injection in fertilized eggs of B6D2/F1 hybrid females. The microinjected oocytes were then reimplanted in B6CBA/F1 hybrid pseudopregnant foster mothers. Three transgenic mice lines were generated and crossed with C57B616/J mice. Genomic DNA was extracted using DNAeasy blood and tissue kit in a QIAcube apparatus (Qiagen, Courtaboeuf). Offspring were followed by PCR using primers rtiMHCP1F (SEQ ID NO: 8) and rtiMHCP1R (SEQ ID NO: 9) and Dynazyme II enzyme (Ozyme, Saint-Quentin-en-Yvelines) as recommended. PCR was performed at least three times per mouse and PCR products were analyzed by acrylamide gel electrophoresis.

Hydrodynamics-Based In Vivo Transfection of the Mouse Liver
DNA was administered as described with minor modifications by a single hydrodynamic injection of 50 µg of plasmid in 2 ml isotonic NaCl in the tail vein of 20- to 24-g mice over 6-8 s.

RNA Extractions and Quality Controls
Total RNA isolated from tissues samples underwent quality check and concentration control as previously described. Total RNA was isolated from cultured H9c2 cardiomyoblasts using RNeasy columns and QIAcube automated apparatus according to the manufacturer's protocol (Ozyme, Saint-Quentin-en-Yvelines).

Real-Time PCR Analysis of Gene Expression
Oligos were designed with PerlPrimer software and synthesized by Eurogentec Company. Real-time PCR was performed as described in a MyiQ™ realtime PCR apparatus (Bio-Rad) using SurePrime kit reagents (MP Biomedicals, Illkirch). Real-time PCR was statistically analyzed with SiginaStat 3 software.

Measurement of $O_2$ Consumption
$O_2$ flows were measured using an OROBOROS Oxygraph-2k (Oroboros Instruments GmbH, Innsbruck, Austria) and standard Oroboros procedures. Calculation of the respiration control index (RC) was done by dividing oxygen consumption in the presence of CCCP by that measured with oligomycin. RC indicates the tightness of the coupling between respiration and phosphorylation.

Reactive Oxygen (ROS) Species Assessment
5-(and-6)-carboxy-2',7'-dichlorofluorescein diacetate (carboxy-DCFDA) was used as recommended by the manufacturer (Life Technologies SAS, Villebon sur Yvette) with a Victor™ X5 2030 multilabel reader (Perkin Elmer, Courtaboeuf)

Caspase-3 Enzymatic Activity Monitoring
Caspase-3 assays were performed using the Caspase-3 Substrate IV Fluorogenic substrate (VWR, Strasbourg) and a Victor™ X5 2030 multilabel reader (Perkin Elmer, Courtaboeuf).

Acyl-CoA Synthetase Activity
Acyl-coA synthetase activity was performed as described in Askari, B. et al., *Diabetes* 56, 1143-1152, (2007).

Cytochrome C Oxydase Activity
Cytochrome C oxydase activity was measured as recommended using Cytochrome c Oxidase Assay Kit Sigma Aldrich (Saint-Quentin-Fallavier) and a Victor™ X5 2030 multilabel reader (Perkin Elmer, Courtaboeuf).

Co-Immunoprecipitation and GST Pull-Down
Co-immunoprecipitation (Co-IP) and GST pull-down were performed in RIPA buffer as described in Harlow, E et al., *Cold spring Harbor Laboratory Press*, (1999).

Confocal Microscopy
Fluorescence detection of Bodipy-Palmitate (Life Technologies SAS, Villebon sur Yvette) was performed on Falcon culture slides (BD Biosciences, Le Pont de Claix). Subconfluent cells were incubated 2 min with Bodipy-Palmitate 1 µM, washed twice in phosphate-buffered saline (PBS) and fixed in PBS containing 4% formaldehyde for 15 min at room temperature followed by 5 min at −20° C. Cells were then washed 3 times in PBS and covered with fluorescent mounting medium and coverslips before being analyzed on a Zeiss LSM 510 confocal microscope (Carl Zeiss Meditec France SAS, Le Pecq).

Transmission Electron Microscopy.
The tissues were fixed in 2% glutaraldehyde in 0.1 M Sorensen phosphate buffer (pH 7.4) for 4 h at 4° C., washed overnight in 0.2 M phosphate buffer and then post-fixed for 1 h at room temperature with 1% osmium tetroxide in 250 mM saccharose and 0.05 M phosphate buffer. The samples were then dehydrated in a series of graded ethanol solutions, followed by propylene oxide, and embedded in an Eponaraldite resin (Embed 812-Araldite 502, Electron Microscopy Sciences). Finally, the tissues were sliced into 70-nm thick sections (Ultracut Reichert Jung) and mounted on 100-mesh collodion-coated copper grids prior to staining with 3% uranyl acetate in 50% ethanol and Reynold's lead citrate. The adhering cells were fixed and washed as above and stained overnight in 2% uranyl acetate. Examinations were carried out on a transmission Hitachi HU12A electron microscope at an accelerating voltage of 75 kV.

Lipid Profiling

Cells or tissues were homogenized in 2 ml of methanol/5 mM EGTA (2:1 v/v) with FAST-PREP (MP Biochemicals). 50 µl was evaporated, the dry pellets were dissolved in 0.2 ml of NaOH (0.1M) overnight, and proteins were measured with the Bio-Rad assay.

Neutral Lipid Molecular Species Analysis.

Lipids were extracted in chloroform/methanol/water (2.5:2.5:2.1, v/v/v), in the presence of the internal standards: 3 µg stigmasterol, 2 µg 1,3-dimyristine, 3 µg cholesteryl heptadecanoate, and 5 µg glyceryl triheptadecanoate. Chloroform phases were evaporated to dryness. Neutral lipids were separated over SPE columns (Macherey Nagel glass Chromabond pure silice, 200 mg). After washing cartridges with 2 ml of chloroform, extract was applied on the cartridge in 20 □l of chloroform and neutral lipids were eluted with 2 ml of a chloroform:methanol solution (90:10, v/v). The organic phase was evaporated to dryness and dissolved in 20 µl of ethyl acetate. 1 µl of the lipid extract was analyzed by gas-liquid chromatography on a FOCUS Thermo Electron system using Zebron-1 Phenomenex fused silica capillary columns (5 m×0.32 mm i.d, 0.50 µm film thickness). Oven temperature was programmed from 200° C. to 350° C. at a rate of 5° C. per min using hydrogen (0.5 bar) as the carrier gas. The injector and the detector were at 315° C. and 345° C., respectively.

Fatty Acid Methyl Ester (FAME) Quantification.

Homogenates were dried in the presence of 2 µg of the internal standard, glyceryl triheptadecanoate, and transmethylated in 1 ml 14% boron trifluoride methanol solution (SIGMA) and 1 ml hexane at 55° C. for 1 h. After addition of 1 ml water to the extract, FAMEs were extracted with 3 ml hexane, evaporated to dryness, and dissolved in 20 µl ethyl acetate. FAMEs (1 µl) were analyzed by gas-liquid chromatography on a Clarus 600 Perkin Elmer system using Famewax RESTEK fused silica capillary columns (30 m×0.32 mm i.d, 0.25 µm film thickness). Oven temperature was programmed from 110° C. to 220° C. at a rate of 2° C. per min and the carrier gas was hydrogen (0.5 bar). The injector and the detector were at 225° C. and 245° C. respectively.

Western Blot

Cardiac or liver tissue was disrupted with mammalian MCL-1 cell lysis kit solution (Sigma Aldrich, Saint-Quentin-Fallavier) in the presence of a mix of protease inhibitors. Procedures were performed according to the manufacturer's protocol. Sixty micrograms of protein was loaded on a 10% polyacrylamide-SDS gel that was blotted on a 0.45 µm nitrocellulose membrane BA85 (Schleicher and Schuell, Ecquevilly, France). Reversible Ponceau S staining was used as a loading control alternative to actin in Western blots. MultiMark Multi-Colored standard (Life Technologies SAS, Villebon sur Yvette) was used to determine molecular mass of the proteins. Nitrocellulose membranes were blocked for 2 h in TBS (7 mM Tris, pH 7.5; 150 mM NaCl) with 0.1% Tween 20 and 3% nonfat dry milk. Hybridization of the anti-ApoO serum was performed in IBS-Tween 0.1% during 2 h. After three washes in TBS-Tween 0.1%, horseradish peroxidase conjugate ($10^{-4}$ dilution) was incubated for 2 h with the membrane in TBS-Tween 0.1% plus 3% nonfat dry milk. Blots were washed three times in Tween-TBS and one time in TBS before hybridizations were revealed with Super-Signal West Pico chemiluminescent substrate according to the manufacturer's protocol (Fisher Scientific SAS, Illkirch, France).

Statistical Analysis and Identification of Differentially Expressed Genes.

All results are depicted as means±SE. Multiple comparisons were analyzed using ANOVA followed, when appropriate, by the Dunnett post hoc test using Statview 4.5 software (Abacus Concepts, Inc., Berkeley, Calif.). Single comparisons were performed using unpaired Student's t-test with a p value ≤0.05 considered as significant.

Results

The results distinguish the interplay between mitochondrial dysfunction and lipotoxicity and demonstrate, for the first time, the implication of the permeability transition pore in lipid metabolism in mouse and human hearts. Moreover, the inventors demonstrate the importance of ApoO as a new signal regulator of mitochondrial function and lipid metabolism. The ApoO-model developed by the inventors represents an original link between impaired mitochondrial heart function and lipid accumulation.

Mouse hearts, constitutively expressing human ApoO at physiological levels (less than 2 times endogenous), exhibited depressed ventricular function, characteristic patterns of systolic dysfunction, and dilated cardiomyopathy. Specifically, cardiac specific ApoO-Tg mice displayed a lengthening of the PR interval and a reduction in fractional shortening and ejection fractions. Transmission electron microscopy (TEM) analysis of longitudinal myocardial sections revealed degenerative changes, such as loss or discontinuity of cristae in mitochondria. Examination of publicly available human heartmicroarray data sets revealed that ApoO mRNA levels fluctuated between 1 to 5 arbitrary units. Pathway analysis using synthetic expression ratios between microarrays with the highest and lowest ApoO expression revealed significant enrichment in various metabolic pathways, the most significant being oxidative phosphorylation and mitochondrial dysfunction. The inventors then designed expression vectors to generate cardiomyoblast transfectants overexpressing ApoO. In vivo fluorescent labeling, as well as studies with protein extracts and subcellular fractions from cardiac myoblasts overexpressing ApoO, revealed a mitochondrial localization for ApoO (FIG. 1).

In vivo fluorescent labeling, as well as studies with protein extracts and subcellular fractions (FIG. 1e, f) from cardiac myoblasts overexpressing ApoO, revealed a mitochondrial localization for ApoO. In silico investigation of the ApoO sequence revealed a putative N-terminal mitochondrial "address label". Deletion of 40 N-terminal residues (ApoOΔ1-40) altered ApoO distribution from the mitochondria to the cytoplasm (FIG. 1g).

Furthermore, hydrodynamics-based in vivo mouse liver transfection by rapid tail vein injection of pTT-hApoO expression vector led to a rise in ApoO mRNA levels (FIG. 2), as evidenced by PCR amplification of the expression vector (FIG. 3A), and increased the level of ApoO protein in isolated mitochondria from hepatocytes (FIG. 3B). In recent studies, ApoO has been proposed to be mitochondrial due to evidence obtained with yeast and *C. elegans* orthologs and through proteomics and confocal microscopy of human cell lines. Interestingly, mutation in the ApoO ortholog of *C. elegans* led to cristae disorganization similar to that observed upon modest ApoO overexpression in mouse heart.

ApoO Increases Mitochondrial Respiration.

In agreement with the human heart transcriptome bioinformatic analysis, the inventors measured a significant increase in the expression of oxidative phosphorylation genes in cardiac myoblasts overexpressing ApoO. This increase was reduced by both N-terminal deletion of ApoO and shApoO treatment of cardiac myoblasts i. The inventors also found an increase in cytochrome C oxidase activity, a mandatory component of the respiratory chain, in both ApoO-Tg hearts and ApoO cells, which displayed a two-fold increase in basal oxygen consumption that was dependent on mitochondrial localization of ApoO and ablated by ApoO shRNA treatment (FIG. 4A). Antimycin, an inhibitor of the quinone cycle, almost completely inhibited oxygen consumption, indicating that most of the respiration being measured is mitochondrial (FIG. 4B). Basal oxygen consumption was partly inhibited by oligomycin in ApoO cells and addition of the uncoupler carbonyl cyanide m-chlorophenyl hydrazone (CCCP) led to a 2-fold increase in oxygen consumption, suggesting that these cells have enhanced electron transport activity. Respiration coupling (RC) calculations confirmed that RC decreases in ApoO cells (FIG. 4C). Thus ApoO has two distinct effects on mitochondrial function: an increase in total respiration and mild uncoupling. These effects were also associated with increases in intracellular reactive oxygen species (ROS) (FIG. 4D). The inventors observed equivalent results with isolated mitochondria from hydrodynamics-based in vivo transfected mouse liver, which displayed a significant increase in oxygen consumption.

ApoO Interacts with Cyclophilin-D and Adenine Nucleotide Translocase.

Proper regulation of the mitochondrial permeability transition pore (MPTP), a known therapeutic target, is essential for mitochondrial respiration and cardiac homeostasis. Given the mitochondrial localization of ApoO and the effects observed on mitochondrial structure and cardiac function with modest ApoO overexpression, the inventors hypothesized that ApoO interacts with proteins implicated in MPTP function. MPTP structure has not yet been fully determined. The MPTP was originally proposed to include cyclophilin-D (CypD) in the matrix, the adenine nucleotide translocase (ANT) in the inner membrane and the voltage-dependent anion channel (VDAC) in the outer membrane. Recently, gene-targeted mice experiments have shown that VDAC was dispensable for MPTP. This pore enables free passage into the mitochondria for molecules and metabolites smaller than 1.5 kDa, including protons thus leading to mitochondrial uncoupling. Blue Native Page and GST-pull down experiments demonstrated an interaction between ApoO and cyclophilin-D and/or ANT (FIGS. 5A and B) and excluded any interaction with VDAC, in agreement with the computational prediction that ApoO localizes in the inner mitochondrial membrane.

To test the functional relationship between ApoO and MPTP, the inventors treated ApoO cells with an MPTP blocker: cyclosporin A (CsA), which bind to cyclophilin D. CsA reversed the effect of ApoO overexpression on mitochondrial respiration (FIG. 5C), confirming that ApoO interacts with cyclophilin-D. The inventors also showed that ApoO alters the kinetics of MPTP opening in the cultured cardiac myoblasts as shown by the mitochondrial calcein-cobalt assay. Calcium retention capacity was also significantly diminished in mitochondria isolated from ApoO-Tg mice hearts.

ApoO-induced opening of MPTP would explain the observed mild mitochondrial uncoupling and enhanced oxygen consumption. Several studies have proposed uncoupling as a mechanism accounting for mitochondrial dysfunction in diabetes. As ApoO mediated regulations were reduced by CsA, a drug targeting cyclophilin D (CypD), the inventors could show that CypD gene knock-down in ApoO cells partially prevents ApoO mediated respiration.

Taken together, the results indicate a role for ApoO in the regulation of mitochondrial function.

ApoO-Induced MPTP Opening Increases Fatty Acid Metabolism and Lipotoxicity.

ApoO is highly expressed in mitochondria-enriched tissues that mainly use fatty acids as an energy source, such as heart and brown adipose tissue. Therefore, the inventors assumed that the ApoO-induced increase in electron transport chain flux, would increase the mitochondrial transport of long-chain fatty acids (LCFAs). In order to provide mitochondria with LCFAs, cells would ultimately increase fatty acid uptake at the plasma membrane.

They measured a rapid accumulation of green fluorescent BODIPY-palmitate in ApoO expressing cells (FIG. 6D) and found that total intracellular fatty acids increased 120% (FIG. 6E). They therefore analyzed whether ApoO could induce the expression of genes involved in fatty acid metabolism. In ApoO cells, fatty acid transporter (CD36 and FATP4) expression and long-chain acyl-CoA synthetase (ACSL) activity were strongly increased, effects that were significantly reversed by treatment with either ApoO shRNA or triacsin C, an ACSL inhibitor (FIG. 6A-C). ACSL and FATP4 catalyze LCFA esterification, allowing lipid channeling. Animal models of cardiac lipotoxicity have been generated by increasing lipid uptake via overexpression of ACSL. To validate our hypothesis, the inventors incubated ApoO cells with a low dose of CsA (200 nM) and showed a significant reduction in intracellular fatty acid levels and especially in the expression of FATP4 (FIGS. 7A and B). Deletion of 40 N-terminal residues or treatment of ApoO cardiac myoblast with shCypD reduced the expression of fatty acid transporters and cellular levels of fatty acids indicating that ApoO-induced MPTP opening affects not only mitochondrial respiration but also fatty acid metabolism (FIGS. 7C and D). The inventors assumed that LCFAs could rapidly enter the mitochondria through carnitine palmitoyltransferase I (CPT1) and the non-specific MPTP (permeable to solutes <1.5 kDa). Similarly, hearts from ApoO-Tg mice displayed a significant increase in fatty acid transporter expression and ACSL activity. In human atrial appendage samples, ApoO expression positively correlated with the expression of CD36, FATP4 and ACSL-3. Microarrays data mining were in accordance with these results and showed that CD36 and FATP2 were also increased in hearts of patients with elevated ApoO expression. These changes should be associated with an increase in peroxisome proliferator-activated receptors (PPARα), transcription factor, known to be involved in lipid uptake and β-oxidation. Indeed, ApoO expression led to increased PPARa mRNA levels in human atrial appendage samples, hearts from ApoO-Tg mice, in vivo transfected mouse liver, and ApoO cells.

When excessive fatty acid uptake exceeds mitochondrial fatty acid oxidative capacity, toxic lipid storage increases, resulting in lipotoxicity. While lipid composition analysis of our model systems revealed that ApoO expression did not significantly modify levels of intracellular triglycerides, the levels of toxic species such as diglycerides were increased in ApoO-Tg hearts and transfected liver (FIG. 8a-d). In human heart samples, endogenous ApoO mRNA levels correlated with diglyceride levels but not with triglyceride levels (FIG. 8e-f). Moreover, palmitate treatment of ApoO cells induced a dramatic intracellular accumulation of diglycerides and did not significantly affect triglyceride levels (FIGS. 7E and F).

Deletion of ApoO 40 N-terminal residues or treatment of ApoO cardiac myoblast with shCypD reduced cellular diglyceride levels. Incubation of ApoO cells with 20 nM CsA significantly reduced intracellular diglyceride levels (FIGS. 7G and H), confirming that ApoO-mediated MPTP opening promotes lipotoxicity.

ApoO Increases Apoptosis.

MPTP opening is a key step in the process of programmed cell death. They hypothesized that ApoO overexpression promotes apoptosis and found positive correlations between mRNA levels for ApoO and the proapoptotic factors Bax in human heart (FIG. 9a). Even with the modest overexpression of ApoO in hearts from ApoO-Tg mice, Bax expression and Caspase-3 activity (FIG. 9b-c) were enhanced. These results were confirmed in vivo with ApoO transfected liver (FIG. 9d-e) and in vitro with ApoO cells, where the increase in expression of Bax and activity of Caspase-3 were significantly reversed by ApoO shRNA treatment (FIG. 9f-g). Moreover, TEM revealed the formation of blebs in the plasma membrane of ApoO cells, indicative of the proapoptotic state. Functional genomics analysis of these cells revealed a massive increase in the expression of genes involved in the regulation of programmed cell death and metabolic pathways. Treatment with low doses of CsA cured ApoO cells that presented a reduction in basal Caspase-3 activity and Bax expression. Indeed, these cells presented characteristic morphological amelioration including a reduction in cell body condensation and cytoplasmic vacuolization. Moreover, ApoO overexpression dramatically amplified the apoptotic effect of increasing doses of palmitate, which moderately increased Caspase-3 activity in control cells (FIG. 9h). Interestingly, palmitate-induced Caspase-3 activity was significantly reduced by treatment with CsA (FIG. 9i). ApoO may target Cyclophylin D and ANT and increase apoptosis and lipotoxicity by modulating MPTP opening. These results suggested a potential link between pathological ApoO overexpression and the induction of mitochondrial dysfunction, which should ultimately trigger mitochondrial biogenesis. Accordingly, expression of ApoO and PPAR-γ co-activator 1α (PGC-1α), a master regulator of mitochondrial biogenesis, are tightly correlated in human right atrial appendage samples from patients undergoing heart surgery and in hearts from ApoO-Tg mice. The inventors assumed that increased mitochondrial synthesis balances the mitochondrial alteration and degradation in autophagosomal vacuoles and multilamellar bodies observed in ApoO-Tg hearts and ApoO cells (FIG. 10 a-d). The inventors hypothesized that ApoO-induced apoptosis and mitochondrial alteration drive the cell in a vicious cycle that ends in cell death. This hypothesis explain the myofibrillar and cardiomyocyte loss observed in ApoO-Tg hearts as evidenced by the inventors by the development of fibrosis and apoptosis. Based on their results, the inventors propose ApoO as a central molecule in the model depicted in FIG. 10e.

The cascade of events illustrated in this figure, originates with ApoO-stimulated MPTP opening. At high expression levels, ApoO enhances the opening rate of the MPTP leading to mild uncoupling, increased respiration, and production of reactive oxygen species (ROS). The activated electron transport chain requires more NADH/FADH$_2$ which generates a mitochondrial metabolic sink (FIGS. 10e1 and 2), since NADH and FADH$_2$ production is mainly generated by β-oxidation of LCFAs in the adult heart. This is supported by the observed induction of β-oxidation in ApoO cells LCFAs enter rapidly into the mitochondria through CPT-1 presumably the open MPTP (FIG. 10e3). Increased expression of LCFAs transporters (FATPs) compensate for the increased mitochondrial consumption (FIG. 10e4). LCFAs uptake exceeds mitochondrial fatty acid oxidative capacity and leads to lipotoxicity, especially in presence of saturated LCFAs such as palmitate. Excess palmitate generates toxic lipid byproducts such as diglycerides (FIG. 10e5). This toxicity can be diminished by the addition of unsaturated lipids, like oleate, which compels palmitate to produce non-toxic triglycerides. ApoO cells treated with both palmitate and oleate displayed a 12-fold decrease in their diglyceride/triglyceride ratio (FIG. 11a-b) and a 2-fold decrease in Caspase-3 activity (FIG. 11c). Thus, apoptosis induced by MPTP opening is increased by lipid uptake. The enhanced oxidative stress and mitochondrial dysfunction increases the expression of genes involved in lipid uptake, β-oxidation, and mitochondrial biogenesis, such as PGC1α and PPARα (FIG. 10e6). Increased ROS levels further stimulate MPTP opening and proton gradient loss, which act together with Bax to release apoptosis inducing factor (AIF) and cytochrome C, leading to cell death (FIG. 10e7). The inventors have shown that all subsequent steps, including lipotoxicity and apoptosis can be reversed by blocking the MPTP. Indeed, CsA not only reduced the respiration rate but also apoptosis, as indicated by the decrease in expression of proapoptotic genes such as Bax and Caspase-3 activity. MPTP blockers also reduced the expression level of fatty acid transporters and reduced lipid accumulation. Thus, the MPTP is involved in fatty acid metabolism.

Obesity and diabetes are forerunners to secondary organ failure through excessive ectopic lipid deposition. This lipotoxicity manifests as cardiomyopathy, myopathy, fatty liver, pancreatitis, hypothyroidism and diabetes. The nature of the signal that leads to sustained lipid uptake in cells remains unknown. Animal lipotoxicity models display evident mitochondrial dysfunction. In these models, fat accumulation has been proposed to precede the reduction in mitochondrial function. However, converse mechanisms have been proposed in which mitochondrial dysfunction plays a more causative role. The inventors brought evidence that lipotoxicity is a consequence and not a cause of mitochondrial dysfunction.

Studies in yeast and *C. elegans* revealed that ApoO orthologs are located within the inner membrane in a mitofilin complex. Mitofilins participate in hetero-oligomeric protein complexes that have been termed Mitochondrial INner membrane Organizing Systems (MINOS, also called MITOS or MICOS). MINOS integrity is required for the maintenance of the characteristic morphology of the inner mitochondrial membrane with an inner boundary region closely apposed to the outer- and cristae membranes. Mitofilin proteins are crucial organizers of mitochondrial architecture. In this work, the inventors showed that at least one protein from this complex, i.e. ApoO, plays a more active role than structural organizer and regulates MPTP opening.

Therefore, physiological role of ApoO in heart could give new insights into the primary pathological process of cardiac dysfunction in diabetes and obesity. This work also establishes a link between the onset of impaired mitochondrial heart function and lipid accumulation via the new mitochondrial actor ApoO.

Example 2: ApoO Induces Apoptosis in a Cancer Cell Line

Materials and Method
Cell Culture and Transfection of U87 Glioblastomas
U87 were obtained from the European Collection of Cell Cultures (Salisbury, England). p y, g) U87 cells were cultured in Dulbecco's modified Eagle medium (Life Technologies SAS, Villebon sur Yvette) adjusted to contain 1.5 g/liter sodium bicarbonate and supplemented with antibiotic-antimycotic solution (Life Technologies SAS, Villebon sur Yvette) and 10% fetal bovine serum (FBS, AbCys s.a., Paris). Cells were plated on 10-cm diameter tissue culture dish and grown in a 5% CO2 incubator at 37° C. with saturating humidity with medium changes every 2 days. U87 glioblastomas were stably transfected by electroporation and pools of transfectants were selected as previously described (Smih et al 2002).

Western Blot Analysis

Cultured cells were resuspended in RIPA buffer (0.15 M sodium chloride, 1% NP-40, 0.5% sodium deoxycholate, 0.1% SDS, 50 mM Tris, pH 8) in the presence of a mix protease inhibitors. The lysate was sonicated 6 s and centrifuged at 6,500 g for 10 min. Twenty micrograms of protein were loaded on a 12% polyacrylamide-SDS gel that was blotted on a 0.45 μm nitrocellulose membrane BA85 (Schleicher and Schuell, Ecquevilly, France). Reversible Ponceau Sstaining was used as a loading control. MultiMark Multi-Colored standard (Life Technologies SAS, Villebon sur Yvette) was used to determine molecular mass of the proteins. Nitrocellulose membranes were blocked for 2 h in TBS (10 mM Tris, pH 8.8, 150 mM NaCl) with 0.1% Tween 20 and 3% nonfat dry milk. The membrane was then hybridized with the desired antibody. To reveal ApoO protein, membrane was incubated with anti-ApoO serum with IBS-Tween 0.1% buffer for overnight at 4° C. After three washes in IBS-Tween 0.1%, horseradish peroxidase conjugated rabbit antibody (Life Technologies SAS, Saint Aubin, France) diluted 100,000-fold was incubated for 2 h with the membrane in TBS-Tween 0.1% plus 3% nonfat dry milk. Blots were washed three times in TBS-Tween 1% and one time in IBS before hybridizations were revealed with SuperSignal West Pico chemilumunescent substrate according to the manufacter's protocol (Fisher Scientific SAS, Illkirch, France). Hybridization and revelation with Calreticulin (Epitomics, Burlingame, USA) antibody was performed according to the manufacter's protocol. Protein immuneband densitometry was quantified with the ImageJ software.

Palmitate Preparation and Caspase-3 Activity Monitoring

Previously transfected glioblastomas with pTT alone or pTT-ApoO were treated with 100 μM palmitate overnight. Palmitate preparation and Caspase-3 activity assays were performed as previously described (Hickson-Bick et al. 2000; Hirota et al. 2006). Caspase-3 activities were measured using the Caspase-3 Substrate IV Fluorogenic substate (VWR, Strasbourg) and a Victor™ X5 2030 multilabel reader (Perkin Elmer, Courtaboeuf).

Results

The inventors have developed U87 transfectant cells overexpressing ApoO (FIG. 12). U87 is a human primary glioblastoma cell line, which was obtained by the inventors for the purpose of the experiments, from the European Collection of Cell Cultures.

The inventors measured and compared the Caspase-3 activity in
control U87 cells (pTT); and
U87 transfectants cells overexpressing ApoO (pTT-ApoO).

The results show a significant increase in the Caspase-3 activity in U87 transfectant cells overexpressing ApoO in comparison with the control U87 cells (FIG. 13), indicating an amplified apoptotic effect. Indeed, as previously mentioned, Caspase-3 activity is proved to be enhanced in apoptotic cells.

Consequently, these results indisputably show that apoptosis is induced in cancerous cell lines overexpressing ApoO, confirming a key role of ApoO in the induction of apoptosis.

These results thus evidence that ApoO is a central target for implementing strategies for treating cancer, especially by inducing apoptosis.

Example 3: ApoO Induces Apoptosis in a Cancer Cell Line

It is now widely admitted that dysregulated metabolism is a hallmark of cancer cells. In addition, it is known that glioblastoma cells use mitochondrial glucose oxidation during aggressive tumor growth.

Further, metabolic differences between the tumor and surrounding brain tissue indicate that metabolic activities constitute a key target for cancer therapy.

As previously mentioned, the inventors have shown here that apolipoprotein 0 (ApoO) enhances mitochondrial respiration, fatty acid metabolism and lipotoxicity.

Further, the inventors decided to investigate the effect of transforming gliobastoma cells so that they express ApoO. For this purpose, glioblastoma cells were transformed with an adeno-associated virus 9 comprising a polynucleotide encoding ApoO.

a) ApoO Induces Glioblastoma Respiration

The inventors compared the oxygen consumption after treating glioblastoma cells with a short hairpin RNA (shApoO) silencing the expression of ApoO.

The inventors have shown that the oxygen consumption is more important in cells which express ApoO in comparison with cells treated with shApoO, i.e. in cells in which said expression is repressed (FIG. 14).

Consequently, the inventors have put in light the fact that ApoO induces glioblastoma respiration.

b) ApoO Induces Lipotoxicity in Glioblastoma

In addition, the inventors have enlighten that:
in gliobastoma cells which do not express ApoO, lipids do not accumulate, even in the presence of palmitate; whereas
in gliobastoma cells which express ApoO, lipid accumulate in the presence of palmitate.

The vesicles of lipids are shown by an arrow in FIG. 15.

These results indicate that the expression or the overexpression of ApoO indisputably induces the lipid accumulation, which is responsible for lipotoxicty.

c) ApoO Promotes Mitochondrial Dysfunction in Glioblastoma and Induces Apotosis

Finally, the inventors have unveiled that the expression or overexpression of ApoO in glioblastoma cells induces the development of abnormal mitochondria.

These findings clearly indicate that ApoO promotes mitochondrial dysfunction in glioblastoma.

Besides, the inventors have confirmed that apoptosis occurs in cells which express ApoO, whereas said result is not found in cells which do not express ApoO (FIG. 16). The phenomena of apoptosis are indicated by an arrow.

Conclusion

These inventors have met the burden to induce overexpression of ApoO by using AAV9 expressing ApoO in glioblastoma cells. The use of adeno-associated virus 9 is highly convenient for delivering a gene in a brain cell, since AAV9 is able to cross the blood brain barrier.

The inventors confirmed that expression or overexpression of ApoO leads to lipotoxicity and mitochondrial dysfunction within the targeted cancerous cell. These phenomena eventually lead to apoptosis of glioblastoma cells.

These results thus confirm that ApoO is a highly promising therapeutic strategy for treating cancer.

The invention claimed is:

1. A method for inducing apoptosis in a cancerous cell comprising a step of administering, in an effective amount to induce apoptosis of said cancerous cell, a compound selected from the group consisting of Apolipoprotein O (ApoO), a polypeptide comprising an ApoO fragment which induces apoptosis comprising at least one of SEQ ID NO: 10, SEQ ID NO: 11, and SEQ ID NO: 12, and mixtures thereof.

2. The method according to claim 1 wherein said method is for treating cancer.

3. A method according to claim 1, wherein said cancerous cell is selected from the group consisting of heart cell, liver cell, bladder cell, brain cell, breast cell, colon cell, rectum cell, endometrium cell, kidney cell, blood cell, epidermis cell, pancreas cell, prostate cell and thyroid cell.

4. A method according to claim 1, wherein said cancerous cell is a brain cancer cell, said brain cancer being selected from brain cancers includes chordomas, craniopharyngiomas, gangliocytomas, gangliomas, anaplastic ganglioglimas, glomus jugulare, meningiomas, pineocytomas, pituitary adenomas, schwannomas, glioma, hemangioblastomas and rhabdoid tumors.

5. A method according to claim 1, wherein said cancerous cell is selected from the group consisting of astrocytes, ependymal cells and oligodendroglial cells.

6. A method according to claim 1, wherein said cancer is glioblastoma.

7. A method according to claim 1, wherein said compound is a human ApoO as depicted in SEQ ID NO: 1.

8. A method according to claim 1, wherein said compound is said polypeptide comprising an ApoO fragment, said fragment having a length between 30 to 190 amino acids.

9. The method according to claim 8, wherein said fragment has a length between 50 and 130 amino acids.

10. The method according to claim 9, wherein said fragment has a length between 70 and 120 amino acids.

11. A method according to claim 1, wherein said compound is said polypeptide comprising an ApoO fragment, said fragment having a length between 8 to 190 amino acids.

12. The method according to claim 11, wherein said fragment has a length between 8 and 100 amino acids.

13. The method according to claim 12, wherein said fragment has a length between 8 and 50 amino acids.

14. A method according to claim 1, wherein said compound is the fragment of ApoO depicted in SEQ ID NO: 12.

15. A method according to claim 1, wherein said compound is ApoO or a fragment thereof comprising at least one of SEQ ID NO: 10, SEQ ID NO: 11, and SEQ ID NO: 12 and further comprising at least the first 40 contiguous amino acids of ApoO.

16. The method according to claim 1, wherein said compound consists of SEQ ID NO: 10, SEQ ID NO: 11, or SEQ ID NO: 12.

17. A method according to claim 1, wherein said compound interacts with mitochondrial permeability transition pore (MPTP), driving MPTP to adopt an open state thereby inducing mitochondrial uncoupling.

18. A method according to claim 1, wherein said compound interacts with Cyclophillin D (CyPD) and/or adenine nucleotide translocase (ANT).

19. A method according to claim 1, wherein said compound increases mitochondrial respiration, increases fatty acid metabolism and induces lipid accumulation within said cancerous cells.

* * * * *

```
                               SEQUENCE LISTING

<160> NUMBER OF SEQ ID NOS: 12

<210> SEQ ID NO 1
<211> LENGTH: 198
<212> TYPE: PRT
<213> ORGANISM: Homo sapiens

<400> SEQUENCE: 1

Met Phe Lys Val Ile Gln Arg Ser Val Gly Pro Ala Ser Leu Ser Leu
1               5                   10                  15

Leu Thr Phe Lys Val Tyr Ala Ala Pro Lys Lys Asp Ser Pro Pro Lys
            20                  25                  30

Asn Ser Val Lys Val Asp Glu Leu Ser Leu Tyr Ser Val Pro Glu Gly
        35                  40                  45

Gln Ser Lys Tyr Val Glu Glu Ala Arg Ser Gln Leu Glu Glu Ser Ile
    50                  55                  60

Ser Gln Leu Arg His Tyr Cys Glu Pro Tyr Thr Thr Trp Cys Gln Glu
65                  70                  75                  80

Thr Tyr Ser Gln Thr Lys Pro Lys Met Gln Ser Leu Val Gln Trp Gly
                85                  90                  95

Leu Asp Ser Tyr Asp Tyr Leu Gln Asn Ala Pro Pro Gly Phe Phe Pro
            100                 105                 110

Arg Leu Gly Val Ile Gly Phe Ala Gly Leu Ile Gly Leu Leu Leu Ala
        115                 120                 125

Arg Gly Ser Lys Ile Lys Lys Leu Val Tyr Pro Pro Gly Phe Met Gly
    130                 135                 140

Leu Ala Ala Ser Leu Tyr Tyr Pro Gln Gln Ala Ile Val Phe Ala Gln
145                 150                 155                 160

Val Ser Gly Glu Arg Leu Tyr Asp Trp Gly Leu Arg Gly Tyr Ile Val
                165                 170                 175

Ile Glu Asp Leu Trp Lys Glu Asn Phe Gln Lys Pro Gly Asn Val Lys
            180                 185                 190

Asn Ser Pro Gly Thr Lys
        195

<210> SEQ ID NO 2
<211> LENGTH: 26
<212> TYPE: DNA
<213> ORGANISM: Artificial
<220> FEATURE:
<223> OTHER INFORMATION: Synthetic Primer

<400> SEQUENCE: 2
cgcggatccg caccgagttt gcagta                                          26

<210> SEQ ID NO 3
<211> LENGTH: 31
<212> TYPE: DNA
<213> ORGANISM: Artificial
<220> FEATURE:
<223> OTHER INFORMATION: Synthetic Primer

<400> SEQUENCE: 3
cgcggatcct tagttccagg tgaattcttc a                                    31

<210> SEQ ID NO 4
<211> LENGTH: 29
```

```
<212> TYPE: DNA
<213> ORGANISM: Artificial
<220> FEATURE:
<223> OTHER INFORMATION: Synthetic primer

<400> SEQUENCE: 4
aagatatcat gttcaaggta attcagagg                                          29

<210> SEQ ID NO 5
<211> LENGTH: 29
<212> TYPE: DNA
<213> ORGANISM: Artificial
<220> FEATURE:
<223> OTHER INFORMATION: Synthetic Primer

<400> SEQUENCE: 5
ttgatatcct tagttccagg tgaattctt                                          29

<210> SEQ ID NO 6
<211> LENGTH: 31
<212> TYPE: DNA
<213> ORGANISM: Artificial
<220> FEATURE:
<223> OTHER INFORMATION: Synthetic Primer

<400> SEQUENCE: 6
cgggatccat gttcaaggta attcagaggt c                                       31

<210> SEQ ID NO 7
<211> LENGTH: 31
<212> TYPE: DNA
<213> ORGANISM: Artificial
<220> FEATURE:
<223> OTHER INFORMATION: Synthetic primer

<400> SEQUENCE: 7
tcccgggctt agttccaggt gaattcttca c                                       31

<210> SEQ ID NO 8
<211> LENGTH: 21
<212> TYPE: DNA
<213> ORGANISM: Artificial
<220> FEATURE:
<223> OTHER INFORMATION: Synthetic primer

<400> SEQUENCE: 8
cctagcccac accagaaatg a                                                  21

<210> SEQ ID NO 9
<211> LENGTH: 20
<212> TYPE: DNA
<213> ORGANISM: Artificial
<220> FEATURE:
<223> OTHER INFORMATION: Synthetic Primer

<400> SEQUENCE: 9
ccccacggac ctctgaatta                                                    20

<210> SEQ ID NO 10
<211> LENGTH: 9
<212> TYPE: PRT
<213> ORGANISM: Homo sapiens

<400> SEQUENCE: 10

Tyr Thr Thr Trp Cys Gln Glu Thr Tyr
1               5
```

```
<210> SEQ ID NO 11
<211> LENGTH: 9
<212> TYPE: PRT
<213> ORGANISM: Homo sapiens

<400> SEQUENCE: 11

Gln Trp Gly Leu Asp Ser Tyr Asp Tyr
1               5

<210> SEQ ID NO 12
<211> LENGTH: 8
<212> TYPE: PRT
<213> ORGANISM: Homo sapiens

<400> SEQUENCE: 12

Tyr Asp Trp Gly Leu Arg Gly Tyr
1               5
```